US008877177B2

(12) United States Patent
Winqvist et al.

(10) Patent No.: US 8,877,177 B2
(45) Date of Patent: Nov. 4, 2014

(54) CHEMOKINE CONTAINING APHERESIS COLUMN AND METHODS OF USE

(75) Inventors: Ola Winqvist, Svankärrsvägen (SE); Graham Cotton, Edinburgh (GB)

(73) Assignee: ITH Immune Therapy Holdings AB, Stockholm (SE)

(*) Notice: Subject to any disclaimer, the term of this patent is extended or adjusted under 35 U.S.C. 154(b) by 360 days.

(21) Appl. No.: 13/063,038

(22) PCT Filed: Sep. 10, 2009

(86) PCT No.: PCT/GB2009/002196
§ 371 (c)(1), (2), (4) Date: May 26, 2011

(87) PCT Pub. No.: WO2010/029317
PCT Pub. Date: Mar. 18, 2010

(65) Prior Publication Data
US 2011/0224645 A1    Sep. 15, 2011

(30) Foreign Application Priority Data
Sep. 10, 2008 (SE) .................................. 0801938-2

(51) Int. Cl.
| A01N 63/00 | (2006.01) |
| A61M 37/00 | (2006.01) |
| B01J 20/30 | (2006.01) |
| B01J 20/32 | (2006.01) |
| B01J 20/26 | (2006.01) |
| B01J 20/28 | (2006.01) |
| C07K 14/52 | (2006.01) |
| C07K 17/06 | (2006.01) |
| C07K 17/10 | (2006.01) |
| A61M 1/36  | (2006.01) |

(52) U.S. Cl.
CPC .......... *A61M 1/3679* (2013.01); *B01J 20/3085* (2013.01); *B01J 20/3272* (2013.01); *B01J 20/3274* (2013.01); *B01J 20/267* (2013.01); *B01J 20/28009* (2013.01); *B01J 20/28016* (2013.01); *B01J 20/3242* (2013.01); *B01J 20/3212* (2013.01); *B01J 2220/58* (2013.01); *B01J 20/28004* (2013.01); *C07K 14/52* (2013.01); *C07K 17/06* (2013.01); *C07K 17/10* (2013.01); *B01J 20/262* (2013.01); *B01J 20/3219* (2013.01); *C07K 14/521* (2013.01)
USPC ........................ 424/93.21; 604/6.03; 604/5.01

(58) Field of Classification Search
None
See application file for complete search history.

(56) References Cited

U.S. PATENT DOCUMENTS

| 5,277,701 A * | 1/1994 | Christie et al. ............... 604/4.01 |
| 6,866,846 B1 | 3/2005 | Heinrich et al. |
| 2004/0077835 A1* | 4/2004 | Offord et al. ................. 530/351 |
| 2010/0025335 A1* | 2/2010 | Shimaki ....................... 210/690 |

FOREIGN PATENT DOCUMENTS

| JP | 11-158076 | 6/1999 |
| WO | WO 00/12113 A2 | 3/2000 |
| WO | WO 02/24307 A2 | 3/2002 |
| WO | WO 2004/026893 A2 | 4/2004 |
| WO | WO 2006/125201 A2 | 11/2006 |
| WO | WO 2007/133147 A1 | 11/2007 |
| WO | WO 2008/038785 A1 | 4/2008 |

OTHER PUBLICATIONS http://pubchem.ncbi.nlm.nih.gov/summary/summary. cgi?sid=24890407&viewopt=PubChem, downloased Jan. 31, 2014.*
Japanese Office Action issued in Appl. No. 2009-509488 pp. 1-6 Jan. 24, 2012.
Engelhardt et al. Therapeutic Targeting of a4-integrins in Chronic Inflammatory Diseases: Tipping the Scales of Risk Towards Benefit *European Journal of Immunology* vol. 35 pp. 2268-2273 Jul. 29, 2005
Kawamura et al. New Method of Leukocytapheresis by the Use of Nonwoven Polyester Fiber Filter for Inflammatory Bowel Disease (abstract only) *Japan Apheresis Academic Society Magazine* vol. 19 (1) pp. 28-33 Feb. 29, 2000.
Wiame, Ilse European Exam Report issued in Application No. 09 785 106.7-1212 *EPO Exam Report* pp. 1-5 Apr. 4, 2012.
CN Office Action issued in related Chinese Application No. 200780016903.7 pp. 1-7 Jul. 11, 2012.
Hiraishi et al. Studies on the Mechanisms of Leukocyte Adhesion to Cellulose Acetate Beads: An In Vitro Model to Assess the Efficacy of Cellulose Acetate Carrier-based Granulocyte and Monocyte Adsorptive Apheresis *Therapeutic Apheresis and Dialysis* vol. 7 (3) pp. 334-340 Jun. 24, 2003.
XP-002618217 *Database UniProtKB/Swiss-Prot* pp. 1-3 Jul. 15, 1998.
Instructions: Pierce Momomeric Avidin Kit—XP-002600558 *Thermo Scientific—Instruction Sheet* pp. 1-2 Jan. 1, 2007.
Calderon et al. Overview and History of Chemokines and Their Receptors *Current Topics in Membranes* vol. 55 pp. 1-47 Jan. 1, 2005.
Emmrich et al. Mobilization of Mucosa Lymphocytes by Leukocytapheresis *Gastroenterology* vol. 130 Supp 2 pp. A-661 Apr. 1, 2006.
Fox et al. The Molecular and Cellular Biology of CC Chemokines and Their Receptors *Current Topics in Membranes* vol. 55 pp. 73-102 Jan. 1, 2005.
Hanai et al. Leukocyte Adsorptive Apheresis for the Treatment of Active Ulcerative Colitis: A Prospective, Uncontrolled, Pilot Study *Clinical Gastroenterology and Hepatology* vol. 1 pp. 28-35 Jan. 1, 2003.
Korber et al. A Case of Crohn's Disease with Increased CD8 T-Cell Activation and Remission during Therapy with Intravenous Immunoglobulins *Scand. J. Gastroenterol* vol. 33 pp. 1113-1117 Jan. 1, 1998.

(Continued)

*Primary Examiner* — Shulamith H Shafer
(74) *Attorney, Agent, or Firm* — Ian J. Griswold; Johnson, Marcou & Isaacs, LLC

(57) ABSTRACT

An apheresis column loaded with a solid support comprises one or more chemokines, in particular biotinylated chemokines, immobilized directly or indirectly on the support, in particular on a support carrying streptavidin. Also disclosed are uses of the column and the support and a method of depleting cells, in particular leukocytes, from the peripheral blood of a person suffering from an inflammatory condition such as Inflammatory Bowel Disease (IBD).

21 Claims, 12 Drawing Sheets

(56) References Cited

OTHER PUBLICATIONS

Niess et al. Chemokines, Chemokine Receptors, and Disease *Current Topics in Membranes*, vol. 55 pp. 1-17 Jan. 1, 2005.

Papadakis, K. Chemokines in Inflammatory Bowel Disease *Current Allergy and Asthma Reports* vol. 4(1) pp. 83-89 Jan. 1, 2004.

Polko et al. Importance of Determination of Lymphocytes in Intestinal Mucosa Biopsy Specimens Using Flow Cyotmetry in the Evaluation of Ulcerative Colitis Activity *Vnitr Lek . (also Medline No. 11968680)* vol. 48 (3) pp. 197-201 Jan. 1, 2002.

Sandborn et al. Biologic Therapy of Inflammatory Bowel Disease *Gastroenterology* vol. 122 pp. 1592-1608 Jan. 1, 2002.

Siosteen, Y.—Swedish Patent Officer International Search Report—PCT/SE07/000459 *International Search Report* pp. 1-7 Sep. 5, 2007.

Thierry et al. Biotinylated Synthetic Chemokines: Their Use for the Development of Nonradioactive Whole-Cell Binding Assays *Journal for Biomolecular Screening* vol. 8 (3) pp. 316-323 Jun. 1, 2003.

Van Deventer, S. J. H. New Biological Therapies in Inflammatory Bowel Disease *Best Practice & Research Clinical Gastroentarology* vol. 17 pp. 119-130 Jan. 1, 2003.

Wiame, Ilse—PCT Officer International Search Report and Written Opinion of Application No. PCT/GB2009/002196 *PCT Search Report* pp. 1-8, Feb. 9, 2011.

Zabel et al. Human G Protein-coupled Receptor GPR-9-6/CC Chemokine Receptor 9 Is Selectively Expressed on Intestinal Homing T-Lymphocytes, Mucosal Lymphocytes, and Thymocytes and Is Required for Thymus-expressed Chemokine-mediated Chemotaxis *The Journal of Experimental Medicine* vol. 190 (9) pp. 1241-1254 Nov. 1, 1999.

Israeli Office Action with English translation of merits—issued in IL Patent Application No. 211587 pp. 1-7 Mar. 11, 2013.

Chinese Office Action issued in related Chinese Application No. 200980141452.9 pp. 1-20 Jan. 30, 2013.

Eurasia Office Action—Application No. 201100452/28 pp. 1-2 Jan. 24, 2013.

Ding et al. Chemokines and their Receptors in Inflammatory Bowel Disease *International Journal of Digestive Disease* vol. 27 (1) pp. 44-46 Feb. 25, 2007.

Wiame, Ilse EPO Office Action—Application No. 09785106.7 pp. 1-5 Jan. 30, 2013.

Wiest, P. Advisory Action in copending U.S. Appl. No. 12/300,401, filed Nov. 12, 2008 pp. 1-3 Dec. 14, 2012.

Wiest, Philip R. Office Action issued in copending U.S. Appl. No. 12/300,501, filed Nov. 12, 2008 pp. 1-14 Nov. 2, 2012.

Wiest, Philip R. Notice of Allowability in copending U.S. Appl. No. 12/300,401, filed Nov. 12, 2008 pp. 1-4 Jan. 29, 2013.

Asahi et al. Blood Purification Therapies Using Dextran Sulfate Cellulose Columns Liposorber and Selesorb *Therapeutic Apheresis and Dialysis* vol. 7 (1) pp. 73-77 Feb. 1, 2003.

EPO Examination Report issued in Appl. No. 07748123.2 *EPO Examination Report* pp. 1-8 Nov. 28, 2011.

Kanai et al. The Logics of Leukocytapheresis as a Natural Biological Therapy for Inflammatory Bowel Disease (XP009135009) *Expert Opinion in Biological Therapy* vol. 6 (5) pp. 453-466 May 1, 2006.

Kelsen et al. Indium-Labelled Human Gut-Derived T Cells from Healthy Subjects with Strong In vitro Adhesion to MAdCAM-1 Show No Detectable Homing to the Gut In vivo *Clinical Experiments In Immunology* vol. 138 pp. 66-74 Oct. 1, 2004.

Kitano et al. Role of LDL Apheresis in the Management of Hypercholesterolaemia *Transfusion Science* vol. 14 pp. 269-280 Jul. 1, 1993.

Lampinen et al. Eosinophil Granulocytes are Activated During the Remission Phase of Ulcerative Colitis *Gut* vol. 54 pp. 1714-1720 Dec. 1, 2005.

Sandborn, William J. Preliminary Data on the Use of Apheresis in Inflammatory Bowel Disease *Inflammatory Bowel Disease* vol. 12 (Suppl. 1) pp. S15-S21 Jan. 1, 2006.

Office Action issued in U.S. Appl. No. 12/300,501 *U.S. Office Action* pp. 1-9 Dec. 22, 2011.

English-language translation of Office Action dated Jul. 2, 2013 for Japanese Patent Application No. 2011-525615, 6 pages.

Pierce Monomeric Avidin Kit, 2007, http://www.piercenet.com/instructions/2160340.pdf.

\* cited by examiner

SEQUENCE LISTING

```
<160> NUMBER OF SEQ ID NOS: 1

<210> SEQ ID NO 1
<211> LENGTH: 75
<212> TYPE: PRT
<213> ORGANISM: Homo sapiens

<400> SEQUENCE: 1

Gly Val Phe Glu Asp Cys Cys Leu Ala Tyr His Tyr Pro Ile Gly Trp
1               5                   10                  15

Ala Val Leu Arg Arg Ala Trp Thr Tyr Arg Ile Gln Glu Val Ser Gly
            20                  25                  30

Ser Cys Asn Leu Pro Ala Ala Ile Phe Tyr Leu Pro Lys Arg His Arg
        35                  40                  45

Lys Val Cys Gly Asn Pro Lys Ser Arg Glu Val Gln Arg Ala Asn Leu
    50                  55                  60

Glu Lys Leu Leu Asp Ala Arg Asn Lys Val Phe
65                  70                  75
```

CHEMOKINE CONTAINING APHERESIS COLUMN AND METHODS OF USE

RELATED PRIORITY APPLICATIONS

This application is a National Stage patent application filed under 35 U.S.C. §371 of International Patent Application No. PCT/GB2009/002196, filed Sep. 10, 2009, which designated the United States of America and which claims priority to Swedish Patent Application No. 0801938-2, filed Sep. 10, 2008. The disclosure of each of the above-identified related applications is hereby fully incorporated herein by reference.

FIELD OF THE INVENTION

The present invention relates to products for and methods of treating inflammatory conditions, such as inflammatory bowel disease, in particular ulcerative colitis (UC) and Crohn's disease (CD), most particularly fulminant ulcerative colitis and Crohn's disease, and a means for the treatment.

BACKGROUND OF THE INVENTION

Fulminant ulcerative colitis is a worsening of ulcerative colitis characterized by a high white blood cell count and severe abdominal pain. At present, patients with fulminant ulcerative colitis are treated with high doses of steroids. In phase III-studies treatment with anti-TNFα has been investigated. Both drugs are general inhibitors of inflammation. They are effective in about 50% of cases but have serious adverse effects. Even if successfully treated fulminant ulcerative colitis has a tendency of recurring.

In patients with fulminant ulcerative colitis not responding to medical treatment prompt surgical intervention is mandatory. Ulcerative colitis is always restricted to the large intestine (colon). As a last measure the colon is resected, and an external ileostoma constructed. After a recovery period of at least 6 months and sometimes further medical treatment of rectal stump inflammation either ileorectal anastomosis or reconstructive surgery with a pelvic pouch will be performed in most patients to restore intestinal continuity. Both procedures entail loose stools about six times daily and disturbances in water- and mineral balances. There may also be fulminant episodes in Crohn's disease (fulminant Crohn's colitis), which are also serious conditions necessitating immediate medical and/or surgical intervention.

While the inflammation can be located in any part of the gastrointestinal tract in patients with Crohn's disease, it is usually confined to the most distal part of the small intestine and the first part of the large intestine (ileocaecal region). Medical treatment cannot cure the disease although anti-inflammatory drugs such as steroids and aza-thioprine relieve symptoms. Surgery with resection of stenotic and fistulating bowel segments is indicated in about 50% of patients; half of them will have recurrences and need further surgery. A method which can specifically turn off the inflammation in IBD and prevent recurrent disease in the individual patient thus is highly warranted.

WO 2008/038785 describes a cell adsorption column to remove cells, particularly activated leukocytes and cancer cells, and cytokines from the blood.

SUMMARY OF THE INVENTION

Inflammatory bowel disease is characterized by inflammation and infiltration of leukocytes in the affected intestine. Chemokines are a class of cytokine molecules involved in cell recruitment and activation in inflammation. Chemokines cause chemotaxis and activation of various subpopulations of cells in the immune system. The activity of chemokines is mediated primarily through tight binding to their receptors on the surface of leukocytes. The present invention is based on the realisation that the interaction between chemokines and cells expressing their receptors may be exploited for the treatment of inflammatory conditions, in particular chronic inflammatory conditions characterised by increased recruitment of chemokine receptor-expressing cells to the site of inflammation. Thus, the invention serves to reduce the recruitment of inflammatory leukocytes to a site of inflammation, which is caused by induction of high levels of expression of inflammatory chemokines. This is achieved using such inflammatory chemokines to capture inflammatory leukocytes from the patient. More specifically, leukocytes and in particular one or more of (activated) T lymphocytes, (activated) monocytes, (activated) neutrophil granulocytes, (activated) eosinophil granulocytes are responsible for the initiation and maintenance of inflammation in IBD, and thus their removal from circulation might reduce and even eliminate such inflammation. By flow cytometry of intestinal biopsy samples from patients with active IBD the present inventors identified (activated) T lymphocytes, monocytes, neutrophil and eosinophil granulocytes; cells that are enriched in the inflammatory site, but also present in circulating peripheral blood.

Thus, the invention provides in a first aspect a solid support comprising one or more chemokines immobilized directly or indirectly on the support to permit removal of a cell expressing the cognate receptor of the chemokine or chemokines, in particular a (n activated) leukocyte as described herein (such as a monocyte or lymphocyte), from the peripheral blood of a patient. The chemokines are inflammatory chemokines, i.e. those induced at high levels by cells or tissues in response to injury or infection (and which serve to recruit inflammatory leukocytes).

In the context of the present invention the term "chemokine" comprises biotinylated or otherwise labeled chemokines. The term "chemokine" also comprises modified and truncated versions of the chemokine with the proviso that the modified or truncated form retains its ability to bind to its cognate receptor (and thus remains functional in the context of the invention). Modifications may be made to improve protein synthesis, for example uniformity of product and yield. Modifications may comprise amino acid additions, substitutions, deletions or other modifications to one or more amino acids in the chemokine. Modifications may comprise substitution of the wild type amino acid with non-natural amino acids such as norleucine (NLeu) and derivatized amino acids such as pyroglutamic acid (pyroGlu). Such modifications may be made to minimize side-product formation during storage and use of the columns of the invention. Modifications may be made to improve labeling, for example inclusion of a polyethylene glycol (PEG) spacer to facilitate biotinylation. The biotinylation and/or conjugation with fluorochromes or other labeling groups of the chemokine is performed in a manner which does not substantially affect the receptor binding capacity. Site specific biotinylation or other labelling is preferred as non-selective labelling of chemokines may compromise receptor binding activity. Biotinylation or other labelling is generally preferred at or towards the C-terminus of the protein as the inventors have found that modifications in this area are generally well tolerated (in terms of a minimal effect on receptor binding capability).

Truncations may involve deletion of either N or C terminal amino acids as appropriate, or both. Typically, the truncated version will retain the residues required for the chemokine to fold correctly, for example to retain a chemokine fold structure, consistent with the requirement that a truncated version must retain the ability to bind to the relevant receptor (expressed by (on the surface of) a leukocyte). Truncated versions may comprise anywhere between 1 and 100 less amino acids, such as 1, 2, 3, 4, 5 etc amino acids, than the wild type amino acid sequence in certain embodiments. Of course, truncated versions may comprise further modification as detailed herein. The modified or truncated version may have 40%, 45%, 50%, 55%, 60%, 65%, 70%, 75%, 80%, 85%, 90%, 95% or more overall amino acid sequence identity with the full length wild type chemokine (where a deletion is counted as a difference in amino acid sequence) in certain embodiments. Over the common sequence between the molecules (i.e the amino acids that have not been deleted), there may be 80%, 85%, 90%, 91%, 92%, 93%, 94%, 95%, 96%, 97%, 98% or 99% amino acid sequence identity in certain embodiments. An example of a chemokine of the invention containing both modifications and a truncation and specifically adapted for use in the invention is described in detail herein. The truncated TECK corresponds to residues 1 to 74 of the full length mature protein (and thus lacks amino acids 75 to 127 and the N-terminal signal peptide of 23 amino acids) and thus retains the chemokine fold. In addition, a methionine to Norleucine substitution is incorporated, to prevent oxidation of the residue during chain assembly. The N terminal glutamine residue is substituted with pyroglutamine to permit uniformity of product during synthesis. Biotinylation is achieved via a PEG spacer at the i-functionality of the lysine residue found at position 72. The amino acid sequence of the linear molecule (i.e. without the PEG spacer and biotin molecule at amino acid 72 shown) comprises, consists essentially of or consists of the amino acid sequence presented as SEQ ID NO: 1. Chemokines of the invention may be synthesised through any suitable means. Preferably, the chemokines are chemically synthesised as this facilitates modification and labelling etc. However, recombinant DNA based approaches may also be employed in combination with appropriate labelling and modification technologies as required. Thus, the invention also provides a nucleic acid molecule encoding a truncated CCL25 protein comprising, consisting essentially of or consisting of amino acids 1 to 74 of (the mature form of) CCL25 (i.e. the form lacking the signal peptide, which comprises the first 23 amino acids). Thus, the protein lacks amino acids 75 to 127 of the mature CCL25 amino acid sequence. The invention also relates to a vector containing such a nucleic acid molecule and a host cell containing the vector. The vector may additionally comprise a suitable promoter operably linked to the nucleic acid molecule, to facilitate transcription of the corresponding mRNA molecule. The host cell may be capable of expressing the protein by transcription and translation of the nucleic acid molecule encoding a truncated CCL25 protein comprising amino acids 1 to 74 of CCL25 (and thus lacks amino acids 75 to 127 and the N-terminal signal peptide of 23 amino acids).

Chemokine receptors are expressed on a range of migratory cells such as lymphocytes, granulocytes and antigen presenting cells, but also on certain non-migratory cells like epithelial cells and fibroblasts. As aforementioned, the chemokines of the invention are immobilised on a solid support in a manner to permit removal of a cell expressing the cognate receptor of the one or more chemokines from the peripheral blood of a patient. The cognate receptor for each of the preferred chemokines of the invention is listed in table 1. In certain instances there may be more than one receptor to which the chemokine can bind. Such properties of the chemokine may advantageously permit more efficient treatment through capture of a range of receptor-expressing cells that contribute to the inflammatory condition. In certain embodiments, the support carries a plurality of chemokines with a view to increasing the capture of a range of pro-inflammatory cells.

The inflammation seen in IBD-patients is maintained by a continuous supply of antigen presenting cells (APCs) and T-cells from the blood circulation to the intestinal mucosa. This continuous accumulation of cells is regulated by chemokines and their receptors. Chemokines are thus molecules involved in the recruitment and activation of various immune cell sub-populations during inflammation. One local chemokine produced in inflamed intestinal mucosa is TECK (Thymus expressed chemokine, also named CCL25). Monocytes and lymphocytes in circulating blood recognize the chemokine via the TECK-receptor; Chemokine Receptor 9 (CCR9). The cells bind to TECK via the CCR9 receptor and start to migrate to the site of intestinal inflammation (1). Upon reaching the inflamed mucosa, the monocytes develop into APCs. Circulating CCR9-expressing T-cells also locate to sites of intestinal inflammation, where they become activated. Ablation of CCR9 or its ligand TECK by genetic deletion or antibody inhibition attenuates the migration of T-cells to the intestine in mouse models (2). The CCR9-TECK interaction seems to play a central role in the migration of monocytes and T-cells to the entire intestinal tract; the small bowel as well as the colon. A recent study verifies the presence of both CCR9 and TECK within the large bowel in healthy and IBD-burdened human intestine. Investigation of colon tissue collected from patients with either CD or UC reveals the presence of CCR9-expressing T-cells through immunohistochemical staining. Furthermore, the presence of the receptor agonist TECK is also observed in the colon (3). In IBD-patients, the rationale is to remove the circulating CCR9-expressing monocytes and T-cells before they reach the intestinal inflammation and thereby reduce the inflammation. By employing a column carrying biotinylated TECK (bTECK) immobilized on a solid support, which entraps CCR9-expressing monocytes and T-cells from the circulation, the constant fuelling of the inflammation should be suppressed, allowing the mucosa to heal. The same rationale may be applied to a number of chemokines involved in the recruitment of leukocytes to the inflamed intestinal regions. For example, IL-8 is secreted by the gut mucosa to attract neutrophils through interaction with the IL-8 receptor. CCR6 regulates Th17 cell migration to the gut and effector T cell balance/distribution in inflamed tissue (14). Thus, CCL20 immobilized on a solid support is also useful in the invention for treating inflammatory conditions such as IBD.

The chemokines of the invention have been selected on the basis of the fact that their expression is found to be upregulated in inflammatory disorders. Moreover, chemokine receptors present on appropriate cell types have been shown to be linked to the incidence of such inflammatory disorders, through recruitment of the receptor-expressing cells to the site of inflammation. Thus, the chemokines of the invention may comprise any one or more of MIP-1a, MIP-1b, MCP-1, MCP-2, MCP-3, MCP-4, TARC, MDC, MIP-3, MIP-3a, MIP3b, MIP-4, 1-309, HCC-1, HCC-2, SLC, IL-8, GROa, GROb, GROg, RANTES, NAP-2, ENA78, GCP-2, IP-10, MIG, I-TAC, SDF, fractalkine, lymphotactin, eotaxin, eotaxin-2, 1-309, BLC, CCL25. Particularly preferred chemokines of the invention comprise MIP-1a, MIP-1b, MIP-3a, MIP-3b, MIP-4, SLC, MCP-1, MCP-2, MCP-3, MCP-4, TARC, MDC, IL-8, IP-10, MIG, I-TAC, fractalkine, CCL-25, RANTES. Most preferred chemokines of the invention are chemokines binding preferably to activated T lymphocytes, in particular MIP-1a, MCP, IP-10, MIG, ITAC, CCL25. By "binding preferably" is meant that the chemokines have a greater tendency to bind to activated T lymphocytes than to non-activated T lymphocytes and/or to other blood cells. In a specific embodiment the chemokine is CCL25. CCL25 binds preferably to cells expressing CCR9, in particular (activated) lymphocytes (CD4 and CD8 lymphocytes) and monocytes (such as CD14-positive monocytes).

Table 1 provides details of certain chemokines useful in the invention, including approved gene symbol (according to the HUGO Gene Nomenclature Committee), name and sequence information. The cognate receptor or receptors for each chemokine is/are also listed.

| Chemokine | Approved Gene Symbol | Approved Gene Name | Location | Sequence Accession IDs | Previous Symbols | Aliases | Receptor |
|---|---|---|---|---|---|---|---|
| MIP-1a | CCL3 | Chemokine (C-C motif) ligand 3 | 17q12 | M23178 NM_002983 | SCYA3 | G0S19-1, LD78ALPHA, MIP-1-alpha | CCR5 |
| MIP-1b | CCL4 | Chemokine (C-C motif) ligand 4 | 17q21-q23 | M23502 NM_002984 | LAG1, SCYA4 | MIP-1-beta, Act-2, AT744.1 | CCR5 |
| MCP-1 | CCL2 | Chemokine (C-C motif) ligand 2 | 17q11.2-q21.1 | BC009716 NM_002982 | SCYA2 | MCP1, MCP-1, MCAF, SMC-CF, GDCF-2. HC11, MGC9434 | CCR2 |
| MCP-2 | CCL8 | Chemokine (C-C motif) ligand 8 | 17q11.2 | X99886 NM_005623 | SCYA8 | MCP-2, HC14 | CCR1, CCR2, CCR3, CCR5 |
| MCP-3 | CCL7 | Chemokine (C-C motif) ligand 7 | 17q11.2-q12 | AF043338 NM_006273 | SCYA6, SCYA7 | MCP-3, NC28, FIC, MARC, MCP3 | CCR1, CCR2, CCR3 |
| MCP4 | CCL13 | Chemokine (C-C motif) ligand 13 | 17q11.2 | AJ001634 NM_005408 | SCYA13 | MCP-4, NCC-1, SCYL1, CKb10, MGC17134 | CCR1, CCR2, CCR3 |
| TARC | CCL17 | Chemokine (C-C motif) ligand 17 | 16q13 | D43767 NM_002987 | SCYA17 | TARC, ABCD-2 | CCR4, CCR8 |
| MDC | CCL22 | Chemokine (C-C motif) ligand 22 | 16q13 | U83171 NM_002990 | SCYA22 | MDC, STCP-1, ABCD-1, DC/B-CK, A-152E5.1, MGC34554 | CCR4 |
| MIP-3 | CCL23 | Chemokine (C-C motif) ligand 23 | 17q11.2 | U58913 NM_005064, NM_145898 | SCYA23 | Ckb-8, MPIF-1, MIP-3, CKb8 | CCR1 |
| MIP-3a | CCL20 | Chemokine (C-C motif) ligand 20 | 2q33-q37 | D86955 NM_004591 | SCYA20 | LARC, MIP-Sa, exodus-1, ST38, CKb4 | CCR6 |
| MIP-3b | CCL19 | Chemokine (C-C motif) ligand 19 | 9p13 | AB000887 NM_006274 | SCYA19 | ELC, MIP-3b, exodus-3, CKb11 | CCR7 |
| MIP-4 | CCL18 | Chemokine (C-C motif) ligand 18 (pulmonary and activation-regulated) | 17q11.2 | Y13710 NM_002988 | SCYA18 | DC-CK1, PARC, AMAC-1, DCCK1, MIP-4, CKb7 | Unknown |
| I-309 | CCL1 | Chemokine (C-C motif) ligand 1 | 17q11.2 | M57506 NM_002981 | SCYA1 | I-309, TCA3, P500, SISe | CCR8 |
| HCC-1 | CCL14 | Chemokine (C-C motif) ligand 14 | 17q11.2 | Z49270 NM_032962 | SCYA14 | HCC-1, HCC-3, NCC-2, SCYL2, CKb1, MCIF | CCR1 |
| HCC-2 | CCL15 | Chemokine (C-C motif) ligand 15 | 17q11.2 | AF031587 NM_004167 | SCYA15 | HCC-2, NCC-3, SCYL3, MIP-5, Lkn-1, MIP-1d, HMRP-2B | CCR7 |
| SLC | CCL21 | Chemokine (C-C motif) ligand 21 | 9p13 | AB002409 NM_002989 | SCYA21 | SLC, exodus-2, TCA4, CKb9, 6Ckine | CXCR1, CXCR2 |

-continued

| Chemo-kine | Approved Gene Symbol | Approved Gene Name | Location | Sequence Accession IDs | Previous Symbols | Aliases | Receptor |
|---|---|---|---|---|---|---|---|
| IL-8 | IL8 | Interleukin 8 | 4q13-q21 | YOO787 | | SCYB8, LUCT, LECT, MDNCF, TSG-1, CXCL8, IL-8, NAP-1,3-10C, MONAP, AMCF-I, LYNAP, NAF, b-ENAP, GCP-1, K60 | CXCR2 |
| GROa | CXCL1 | Chemokine (C-X-C motif) ligand 1 (melanoma growth stimulating activity, alpha) | 4q13.3 | J03561 | MGSA, GRO1, FSP | SCYB1, GROa, MGSA-a, NAP-3 | CXCR2 |
| GROb | CXCL2 | Chemokine (C-X-C motif) ligand 2 | 4q13.3 | M36820 NM_002089 | GRO2 | SCYB2, GROb, MIP-2a, MGSA-b, CINC-2a | CXCR2 |
| GROg | CXCL3 | Chemokine (C-X-C motif) ligand 3 | 4q21 | M36821 | GRO3 | SCYB3, GROg, MIP-2b, CINC-2b | CCR1, CCR3, CCR5 |
| RANTES | CCL5 | Chemokine (C-C motif) ligand 5 | 17q11.2-q12 | AF043341 NM_002985 | D17S136E, SCYA5 | RANTES, SISd, TCP228, MGC17164 | CXCR2 |
| NAP-2 | PPBP | Pro-platelet basic protein (chemokine (C-X-C motif) ligand 7) | 4q12-q13 | M54995 NM_002704 | THBGB1 | SCYB7, TGB, NAP-2-L1, LA-PF4, MDGF, LDGF, Beta-TG, CTAP3, CXCL7, PBP, b-TG1, TGB1, CTAPIII, NAP-2 | CXCR2 |
| ENA-78 | CXCL5 | Chemokine (C-X-C motif) ligand 5 | 4q13.3 | X78686 NM_002994 | SCYB5 | ENA-78 | CXCR2 |
| GCP-2 | CXCL6 | Chemokine (C-X-C motif) ligand 6 (granulocyte chemotactic protein 2) | 4q13.3 | U83303 NM_002993 | SCYB6 | GCP-2, CKA-3 | CXCR2 |
| IP-10 | CXCL10 | Chemokine (C-X-C motif) ligand 10 | 4q21 | X02530 | INP10, SCYB10 | IFI10, IP-10, crg-2, mob-1, C7, gIP-10 | CXCR3 |
| MIG | CXCL9 | Chemokine (C-X-C motif) ligand 9 | 4q21 | X72755 | CMK, MIG | SCYB9, Humig, crg-10 | CXCR3 |
| I-TAC | CXCL11 | Chemokine (C-X-C motif) ligand 11 | 4q21 | U66096 | SCYB9B, SCYB11 | H174, b-R1, I-TAC, IP-9 | CXCR3 CXCR7 |
| SDF | CXCL12 | Chemokine (C-X-C motif) ligand 12 (stromal cell-derived factor 1) | 10q11.1 | L36033 NM_000609 | SDF1A, SDF1B, SDF1 | SCYB12, SDF-1a, SDF-1b, PBSF, TLSF-a, TLSF-b, TPAR1 | CXCR4 CXCR7 |
| Fractal-kine | CX3CL1 | Chemokine (C-X3-C motif) ligand 1 | 16q13 | U84487 NM_002996 | SCYD1 | NTN, C3Xkine, ABCD-3, CXC3C, CXC3, fractalkine, neurotactin | CX3CR1 |
| Lympho-tactin | XCL1 | Chemokine (C motif) ligand 1 | 1q24.2 | D43768 NM_002995 | LTN, SCYC1 | LPTN, ATAC, SCM-1a, SCM-1, lymphotactin | XRC1 |

-continued

| Chemokine | Approved Gene Symbol | Approved Gene Name | Location | Sequence Accession IDs | Previous Symbols | Aliases | Receptor |
|---|---|---|---|---|---|---|---|
| Eotaxin | CCL11 | Chemokine (C-C motif) ligand 11 | 17q21.1-q21.2 | AB063614 NM_002986 | SCYA11 | Eotaxin, MGC22554 | CCR3 |
| Eotaxin-2 | CCL24 | Chemokine (C-C motif) ligand 24 | 7q11.23 | U85768 NM_002991 | SCYA24 | Ckb-6, MPIF-2, eotaxin-2, MPIF2 | CCR3 |
| BLC | CXCL13 | Chemokine (C-X-C motif) ligand 13 | 4q21 | AJ002211 | SCYB13 | BLC, BCA-1, BLR1L, ANGIE, ANGIE2 | CXCR5 |
| CCL25 | CCL25 | Chemokine (C-C motif) ligand 25 | 19p13.2 | U86358 NM_005624 | SCYA25 | TECK, Ckb15 | CCR9 |

The chemokines of the invention can be biotinylated by methods known in the art such as described in WO 00/50088 A2, which is incorporated herein by reference. As indicated above, site-specific labelling of the chemokines of the invention is preferable, although any labelling technique which does not significantly affect the receptor-binding capacity of the chemokine may be employed. Various site-specifically biotinylated chemokines and native chemokines are available commercially, for instance from Almac, Craigavon, UK. In specific embodiments the one or more chemokines are biotinylated via a spacer group. The spacer may be employed to prevent the biotin group from impacting on the activity of the chemokine, in particular binding of the chemokine to its cognate receptor. Any suitable spacer that facilitates retention of receptor binding properties of the chemokine may be employed in the invention. In specific embodiments, the spacer is a polyethylene glycol (PEG) spacer. PEG has been shown herein to be an effective spacer permitting attachment of biotin to the chemokine (which can then be immobilized on the solid support through interaction with streptavidin) without compromising receptor binding capability.

Solid support materials for immobilizing the chemokines of the invention are known in the art. A useful support material is one that does not activate blood cells, in particular lymphocytes, so as to make them coagulate or adhere to the support. It is advantageous to use a support treated with an agent to provide it with anti-coagulation properties, in particular a heparinized support. Alternatively, the blood of the patient may be treated with an anti-coagulant such as heparin prior to application to the support. Useful support materials comprise high molecular weight carbohydrates, in particular carbohydrates having a molecular weight of 100 kDa or more, such as agarose, in particulate form, optionally cross-linked, and cellulose. Other preferred support materials are polymers, such as carboxylated polystyrene, and glass. The support of the invention is preferably in the form of particles or fibres. The support particles may have regular form, such as spheres or beads, or irregular form. They may be porous or non-porous. A preferred average particle size of the support is from 50 µm to 2 mm. Methods for immobilizing chemokines on a solid support are known in the art. A chemokine can be immobilized on the support in a direct or indirect manner. Direct immobilization can be by means of a suitable linker. A preferred method of indirect immobilization of a chemokine relies upon the interaction between biotin and avidin molecules. Thus, biotinylation of the chemokine and use of streptavidin immobilized on the solid support allows reliable attachment of the chemokines to the solid support. Specifically, the method may comprise providing the chemokine in biotinylated form, providing a solid support having streptavidin immobilized on its surface, contacting the support with an aqueous solution of the biotinylated chemokine, and rinsing the support with an aqueous solvent. In addition, antibody-antigen interactions may also be utilised for indirect immobilisation of chemokines onto a support. In such embodiments the support may be derivatised with an antibody or fragment or derivative thereof, which has known affinity for a particular peptide sequence or small molecule hapten. Incorporating the peptide sequence or the hapten onto or into the chemokine facilitates immobilisation onto a solid support coated with the corresponding antibody or fragment or derivative thereof. Thus, the chemokine may be modified to include the peptide sequence or hapten into the linear molecule or may be added as a side chain or label. Any suitable antibody-antigen pair may be employed. The antibody fragment or derivative may be any fragment or derivative that retains specific binding affinity for the appropriate antigen. Examples include Fab, scFV, VH domains, nanobodies, heavy chain antibodies and humanized version of non-human antibodies etc. Other high affinity interactions can be utilised for immobilisation of chemokines, as long as the chemokine can be derivatised with one of the interacting partners and the solid support derivatised with the other interacting partner without loss of binding activity (i.e. binding of the chemokine to its cognate receptor).

Alternatively chemokines can be immobilised directly onto a solid support using bioconjugation techniques established in the field. For example direct immobilisation of proteins onto cyanogen bromide activated solid supports via amino functionalities within the primary sequence of the protein. Alternatively, sulphydryl functionalities within proteins can be used to directly immobilise the protein to alkyl halide derivatised supports or supports containing free thiol functionalities. In further embodiments, proteins containing α-thioester functionalities can be directly immobilised on supports containing 1,2 amino thiol moieties (eg N-terminal cysteine) using the native chemical ligation reaction. Alternatively proteins modified with ketones and aldehydes can be immobilised on solid supports derivatised with hydrazinyl, hydrazide and aminoxy functionalities using hydrazone/oxime bond forming ligation reactions (and vice versa). Alternatively 'Click' chemistry can be used to immobilise proteins onto solid supports, whereby the protein and the support are derivatised with the appropriate mutually reactive chemical functionalities (azides and alkynes). In other embodiments Staudinger ligation chemistry can be used to immobilise appropriately derivatised proteins onto the appropriately derivatised solid supports.

According to the present invention is disclosed an apheresis column loaded with the solid support of the aforementioned kind comprising one or more chemokines immobilized thereon. The column is loaded with a solid support comprising one or more chemokines immobilized directly or indirectly on the support to permit removal of a cell expressing the cognate receptor of the chemokine or chemokines, in particular a (n activated) leukocyte as described herein (such as a monocyte or lymphocyte), from the peripheral blood of a patient. According to a preferred embodiment of the present invention the apheresis column is loaded with a support comprising streptavidin immobilized on the support and one or more biotinylated chemokines bound to the streptavidin on the support. It is preferred for the support to be a high-molecular weight carbohydrate, optionally cross-linked, such as agarose. By "loaded" is meant that the column carries or contains the solid support in a manner such that (peripheral) blood can flow through the column in contact with the solid support. Thus, the solid support provides a matrix within the column through which blood flows, in continuous fashion in certain embodiments.

The column of the invention is thus used to carry the support which permits removal of cells expressing the cognate chemokine receptor from a blood sample. More specifically, the column can be used to remove one or more (activated) leukocytes in particular one or more of (activated) T lymphocytes, (activated) monocytes, (activated) neutrophil granulocytes, (activated) eosinophil granulocytes from the peripheral blood of a (n IBD) patient. Depending on the cell profile of individual patients, specific chemokines are selected for the preparation of the support to specifically remove such T lymphocytes, monocytes, neutrophil and eosinophil granulocytes, or other activated kind of cells involved in intestinal inflammation.

Thus, the invention also provides a method of removing cells, such as leukocytes, expressing a corresponding chemokine receptor, such as one or more of (activated) T lymphocytes, (activated) monocytes, (activated) neutrophil granulocytes, (activated) eosinophil granulocytes from the peripheral blood of a patient, in particular of a patient suffering from an inflammatory disorder, more specifically inflammatory bowel disease (IBD), comprising: contacting collected peripheral blood with one or more chemokines immobilized on a solid support for a period of time sufficient to make said cell adhere to the support; and separating the blood depleted in regard of said cell from the support. This method may be an ex vivo or in vitro method. In some embodiments, however, the method further comprises, prior to the contacting step, collecting peripheral blood from the patient. In a further embodiment, the method further comprises, following the separation step, infusing the depleted blood to the patient. This is then a complete leukapheresis treatment method. Thus, a leukaphereis method comprises collecting peripheral blood from the patient; contacting the collected peripheral blood with one or more chemokines immobilized on a solid support for a period of time sufficient to make said cells expressing a corresponding chemokine receptor, such as one or more leukocytes, in particular (activated) T lymphocytes, (activated) monocytes, (activated) neutrophil granulocytes, or (activated) eosinophil granulocytes adhere to the support; separating the blood depleted (in regard) of said cells expressing a corresponding chemokine receptor, such as one or more leukocytes, in particular (activated) T lymphocytes, (activated) monocytes, (activated) neutrophil granulocytes, (activated) eosinophil granulocytes from the support; and infusing the depleted blood to the patient.

The peripheral blood may be continuously collected from the patient. Similarly, the depleted blood may be continuously infused to the patient, through use of an appropriate circuit as described herein. Thus, the support may be disposed in a column through which the blood is made to flow. This may be achieved using a suitable pump for example. Blood flow through the column enables the chemokines immobilized on the solid support to capture the leukocytes expressing the receptor, thus depleting them from the blood and preventing their contribution to the inflammatory condition.

Thus, in general terms the invention provides for use of the column or the support of the invention in the treatment of an inflammatory disorder such as IBD or in the treatment of a disease characterized by the presence of cells (specifically leukocytes) expressing a corresponding chemokine receptor, such as one or more of (activated) T lymphocytes, (activated) monocytes, (activated) neutrophil granulocytes, (activated) eosinophil granulocytes in the peripheral blood of a diseased person. The invention also provides a chemokine for use in therapy, in particular for the treatment of an inflammatory disorder such as IBD, wherein the chemokine is immobilized on a solid support. Likewise, the invention relates to the use of a chemokine in the manufacture of a medicament for the treatment of an inflammatory disorder such as IBD, wherein the chemokine is immobilized on a solid support.

All embodiments described in respect of the support and column of the invention apply to these aspects mutatis mutandis and are not repeated for reasons of conciseness.

According to the invention there is also disclosed a method of producing a magnetic streptavidin-coated microbead complexed with a biotinylated chemokine. The method comprises providing a magnetic streptavidin-coated microbead suspended in an aqueous solvent, providing an aqueous solution of a biotinylated chemokine, mixing the aforementioned suspension and solution, incubating the mixture, separating, optionally by magnetic means, the magnetic streptavidin-coated microbead complexed with a biotinylated chemokine formed, and washing the magnetic streptavidin-coated microbead complexed with a biotinylated chemokine with an aqueous solvent.

The magnetic streptavidin-coated microbead complexed with a biotinylated chemokine of the invention can be used for separating blood cells having (expressing) corresponding chemokine receptors from blood cells lacking such receptors. It is preferred for the separation to be carried out on peripheral blood by a magnetic separator. According to a preferred aspect of the invention, after separation, the peripheral blood is re-infused to the person from which it had been obtained.

The methods and medical uses of the invention thus can be tailored to the need of individual patients or groups of patients. By removing from the circulation cells activated towards intestinal mucosal cells an important factor in the inflammatory process of IBD can be controlled. The method of the invention is particularly effective in treating or reversing ulcerative colitis or Crohn's disease, in particular fulminant (ulcerative) colitis or fulminant Crohn's disease.

The methods and medical uses of the invention can also be used to treat patients with Crohn's disease by removing cells, and in particular leukocytes, expressing a corresponding chemokine receptor, such as (activated) T-cells, (activated) monocytes, (activated) neutrophils, (activated) eosinophils, or other cell types activated towards antigen(s) located deeper in the intestinal wall.

In a more general realization of the invention, the column of the invention or the support of the invention is used in the treatment of a disease characterized by the presence of cells and in particular leukocytes expressing a corresponding chemokine receptor, such as one or more of (activated) T lymphocytes, (activated) monocytes, (activated) neutrophil granulocytes, (activated) eosinophil granulocytes in the peripheral blood of a diseased person.

The invention will now be described in more detail by reference to the following non-limiting embodiments and examples:

DESCRIPTION OF PREFERRED EMBODIMENTS

Materials and Methods

Isolation of Peripheral Blood Leukocytes.

Heparinized peripheral blood from healthy blood donors or IBD patients was fixed with 4% paraformaldehyde for 4 minutes, hemolyzed for 15 minutes with a 0.83% ammonium chloride solution and washed twice in FACS buffer to obtain a suspension of blood leukocytes.

Chemokines.

The leukocytes were incubated for 30 min in the dark at 4° C. with the following biotinylated and Alexa647 Fluor® labeled chemokines: CCL25 (in concentrations of 0.1 ng/μL, 0.5 ng/μL and 5 ng/μL), MIP-1α or MCP-1 (in concentrations 10 ng/μL and 50 ng/μL). The cells were then washed with FACS-buffer and analyzed by flow cytometry. All chemokines used in the Examples were provided by Almac Sciences Scotland Ltd, Edinburgh, Scotland.

Flow Cytometry Assay.

The flow cytometry assay was performed on a two laser FACS Calibur cytometer (BD Immunocytometry systems, San Jose, Calif., USA). Ten thousand cells were counted and analysed in each sample. For data analyses, Cell Quest Pro software from Becton Dickinson was used.

Example 1

Binding of Monocytes to MIP-1α

Figure 1A:
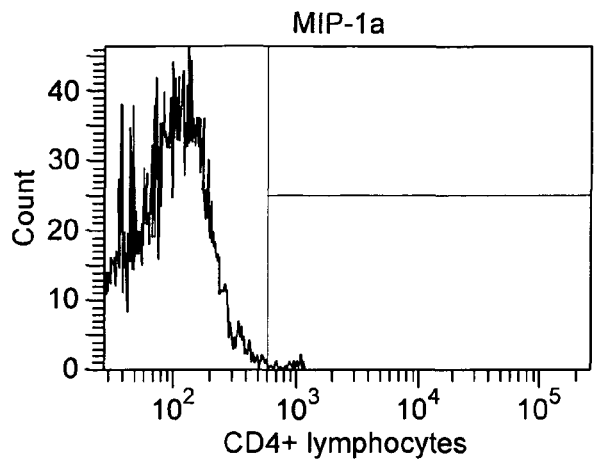
FIGS. 1a, 1b & 1c—the binding of biotinylized MIP-1α by CD4+, CD8+ T-cells and CD14+ monocytes respectively, obtained from peripheral blood of a healthy donor.
Figure 1B:
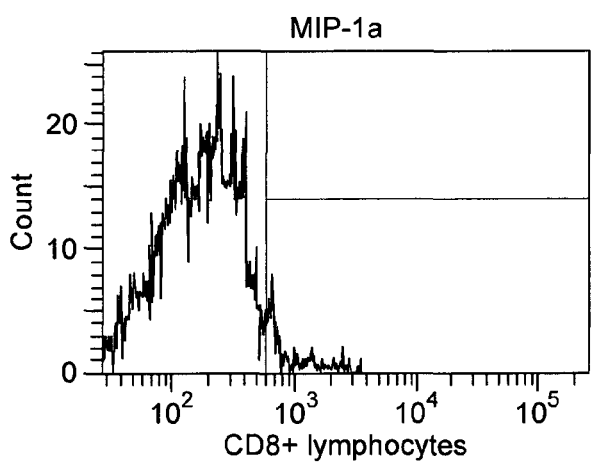
Figure 1C:
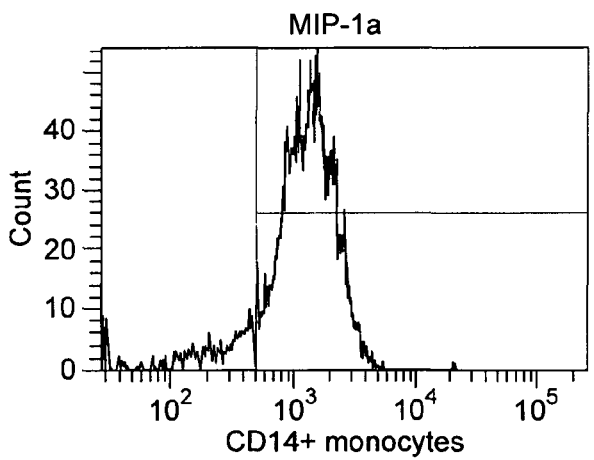

In the experiment with biotinylated MIP-1α it was found that about 90% of the monocytes obtained from peripheral blood of healthy donors had bound to the cytokine after 30 min of incubation (FIG. 1c), whereas CD4+ and CD8+ lymphocytes had not bound (FIGS. 1a and 1b).

Example 2

Binding of Monocytes to MCP-1

Figure 1D:
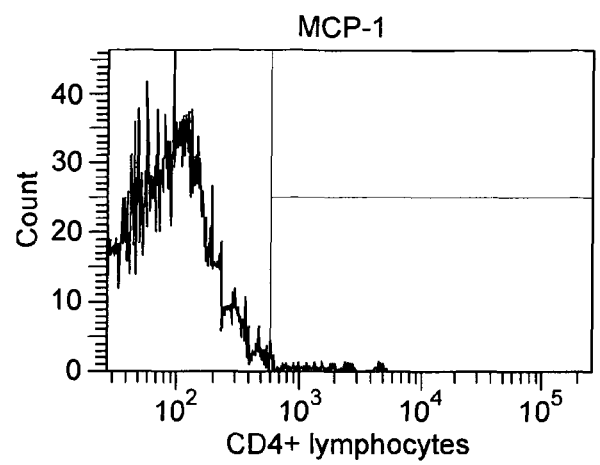
FIGS. 1d, 1e & 1f—the binding of biotinylized MCP-1 by CD4+, CD8+ T-cells and CD14+ monocytes respectively, obtained from peripheral blood of a healthy donor.
Figure 1E:
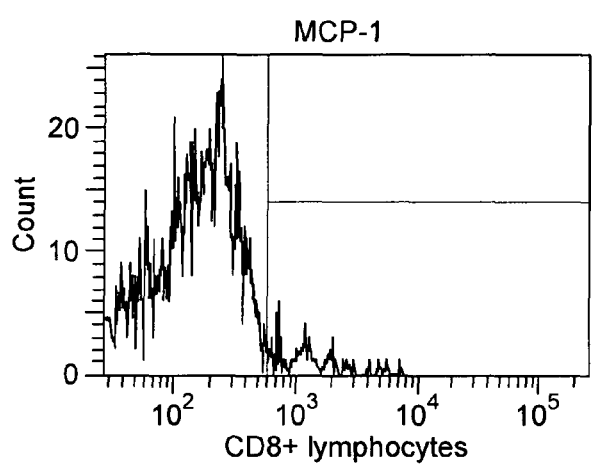
Figure 1F:
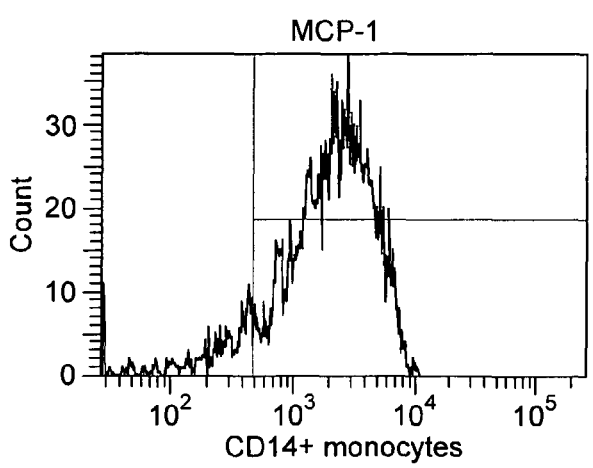

In the experiment with biotinylated MCP-1 it was found that about 90% of the monocytes obtained from peripheral blood of healthy donors had bound to the cytokine after 30 min of incubation (FIG. 1f, whereas CD4+ and CD8+ lymphocytes had not bound (FIGS. 1d and 1e).

Example 3

Affinity of Blood Cells to CCL25

Figure 2A:
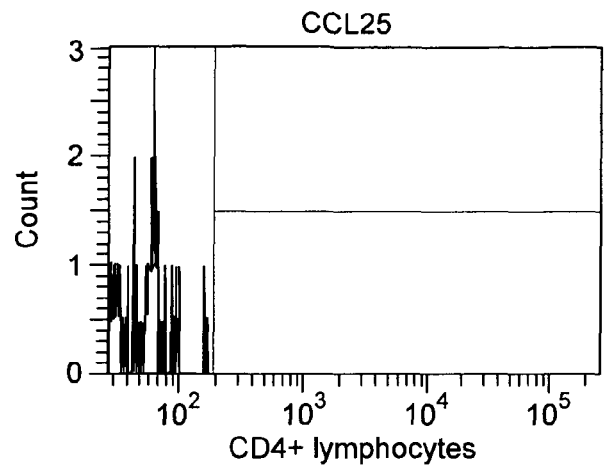
FIGS. 2a, 2b & 2c—the binding of biotinylized CCL25 by CD4+, CD8+ T-cells and CD14+ monocytes respectively, obtained from peripheral blood of a healthy donor.
Figure 2B:
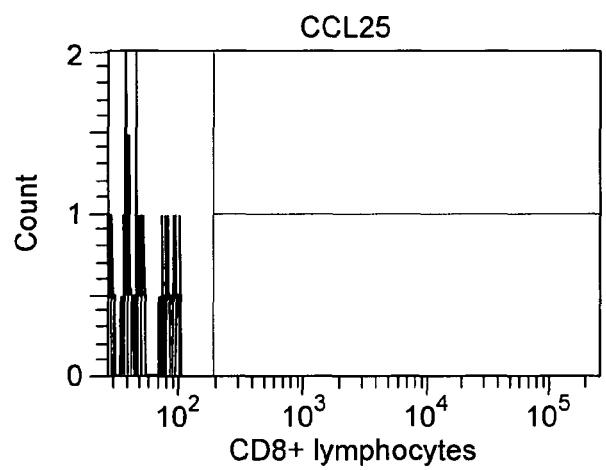
Figure 2C:
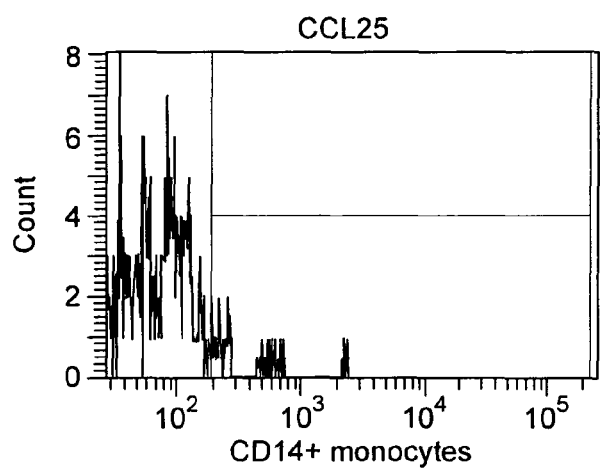
Figure 2D:
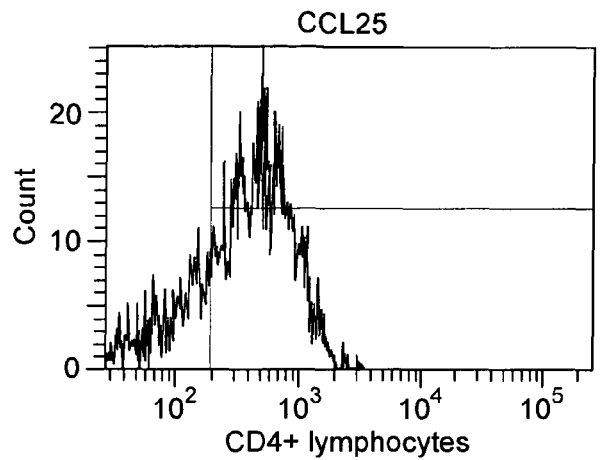
FIGS. 2d, 2e & 2f—the binding of biotinylized CCL25 by CD4+, CD8+ T-cells and CD14+ monocytes respectively, obtained from peripheral blood of a patient with CD.
Figure 2E:
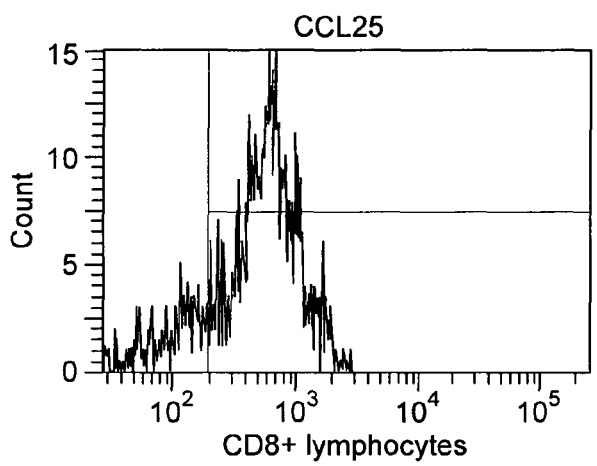
Figure 2F:
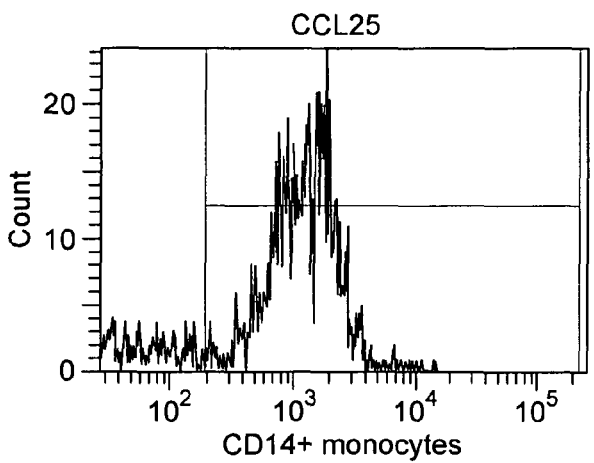

In the experiment with biotinylated CCL25 it was found that neither T-cells (CD4+ lymphocytes; CD8+ lymphocytes) nor monocytes (CD14+ monocytes) from the peripheral blood of a healthy donor (FIGS. 2a, 2b and 2c) bound to the biotinylated chemokine. In contrast, about 80% of the CD8+ lymphocytes and about 90% of the CD4+ lymphocytes and the monocytes from a patient with Crohn's disease bound to CCL25 (FIGS. 2d, 2e and 2f).

Example 4

Affinity of Blood Cells to Biotinylated IL-8

Figure 3A:
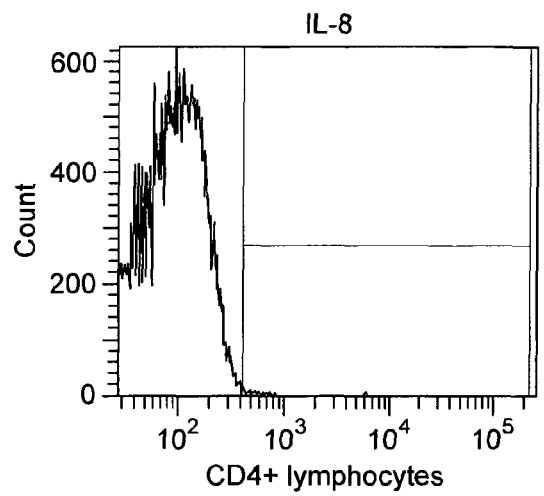
FIGS. 3a, 3b & 3c—the binding of IL-8 by CD4+, CD8+ T-cells and CD16+ monocytes respectively, obtained from peripheral blood of a healthy donor.
Figure 3B:
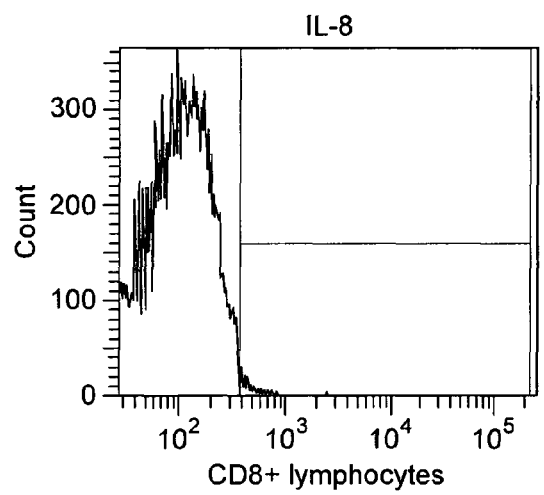
Figure 3C:
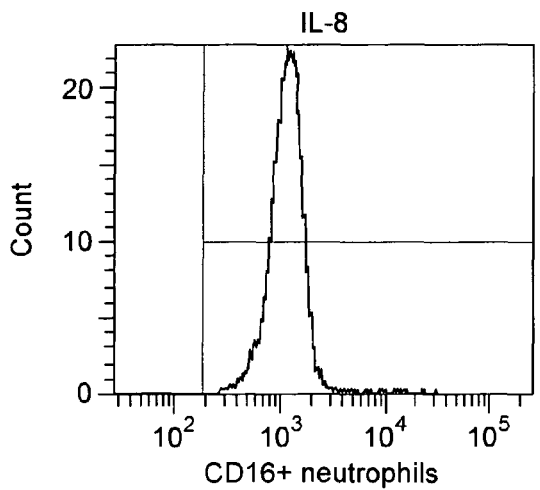

In FIG. 3 the binding to biotinylated IL-8 (CXCL8) of CD4+ lymphocytes (FIG. 3a), CD8+ lymphocytes (FIG. 3b) and CD16+ neutrophils (FIG. 3c) obtained from healthy donors is shown. After 30 min of incubation all CD16+ neutrophils bound to IL-8. In contrast no binding was observed with CD4+ lymphocytes and CD8+ lymphocytes.

Example 5

Preparation of a Chemokine Column for Blood Cell Apheresis

To streptavidin cross-linked agarose (ProZyme, San Leandro, Calif., U.S.A.) beads in the range from 75 μm to 300 g suspended (200 ml, ~50%, v/v) in an aqueous solution of 25 mM sodium phosphate (pH 7.0) and 150 mM NaCl was added a solution of 75 μg biotinylated MIP-1α (Almac Sciences) in the same buffer at 22° C. and slowly stirred by hand for 3 min. After standing for another 20 min, the support was filtered off, washed thrice with neutral aqueous sodium phosphate/sodium chloride and filled into a glass column (i.d. 25 mm, length 12 cm).

Example 6

Separation of Monocytes from Peripheral Blood of a Healthy Donor with the Chemokine Column of Example 6

Heparinized peripheral blood from a healthy male donor was analyzed by flow cytometry for CD4+ lymphocytes, CD8+ lymphocytes and CD14 monocytes. 100 ml of the blood was filtered through the column at a rate of about 8 ml per min and washed with FACS buffer. The filtered blood was analyzed for the same cells. It was found that about 95% of the monocytes had been retained by the column whereas more than 90% each of CD4+ and CD8+ lymphocytes had been recovered.

Example 7

Preparation of Streptavidin Conjugated Magnetic Beads Complexed with Biotinylated MIP-1α

An aqueous suspension of streptavidin conjugated magnetic beads (MagCellect Streptavidin Ferrofluid, 1 ml; R&D Systems, Minneapolis, Minn., U.S.A.) was mixed with 30 μg of MIP-1α (Almac Sciences) in 50 ml of 25 mM sodium phosphate (pH 7.0) and 150 mM NaCl and slowly stirred for 1 hour. The particles were washed thrice with 20 ml portions the same solvent and stored in suspension at 4° C.

Example 8

Separation of CD14+ Monocytes from Peripheral Blood of a Healthy Donor with the Streptavidin Magnetic Beads of Example 8

100 ml of heparinized blood from the healthy donor of Example 7 was mixed with the streptavidin conjugated magnetic beads complexed with biotinylated MIP-1α and slowly stirred for 40 min. The particles were separated from the blood by a magnetic separator, and the blood analyzed for CD14+ monocytes and CD4+ and CD8+ lymphocytes. While essentially no CD14+ monocytes could be detected, CD4+ and CD8+ lymphocytes were present in roughly the original amounts.

Example 9

Tailored Leukapheresis

Figure 4:
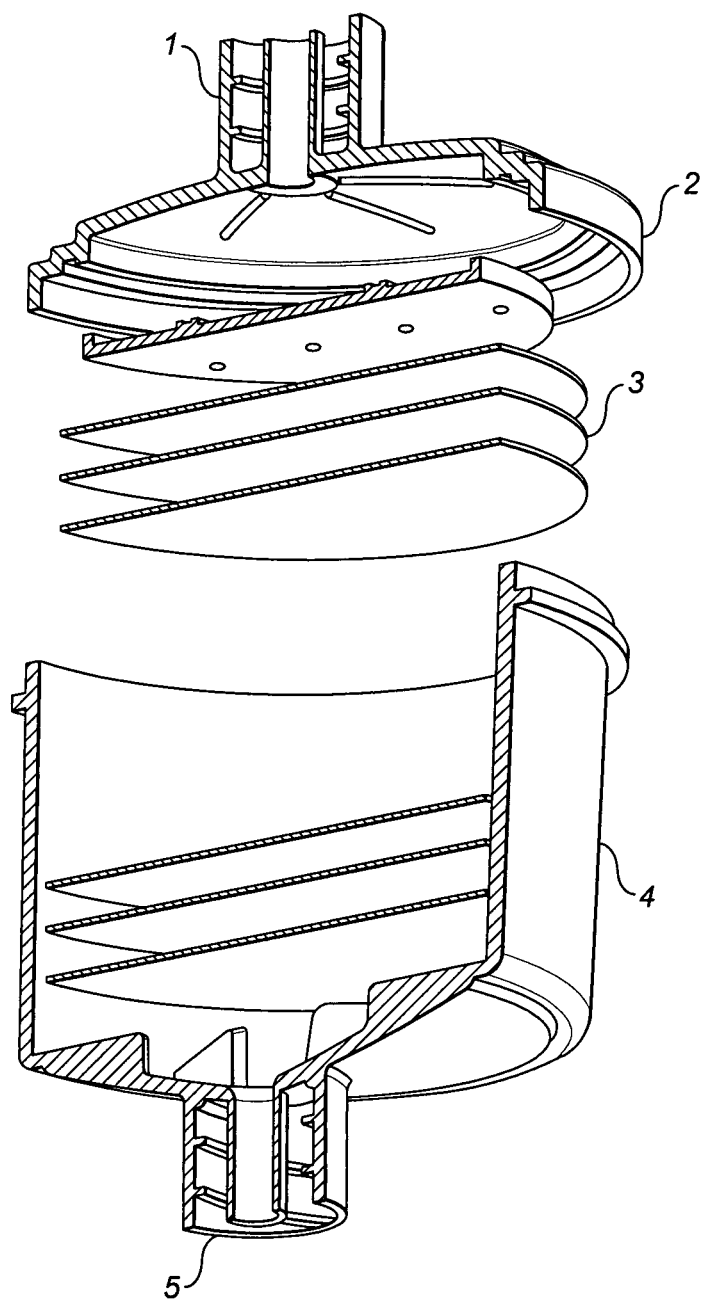
FIG. 4—The plastic house and top showing the distribution plate (2) and safety filter units (3 and 4).
Figure 5:
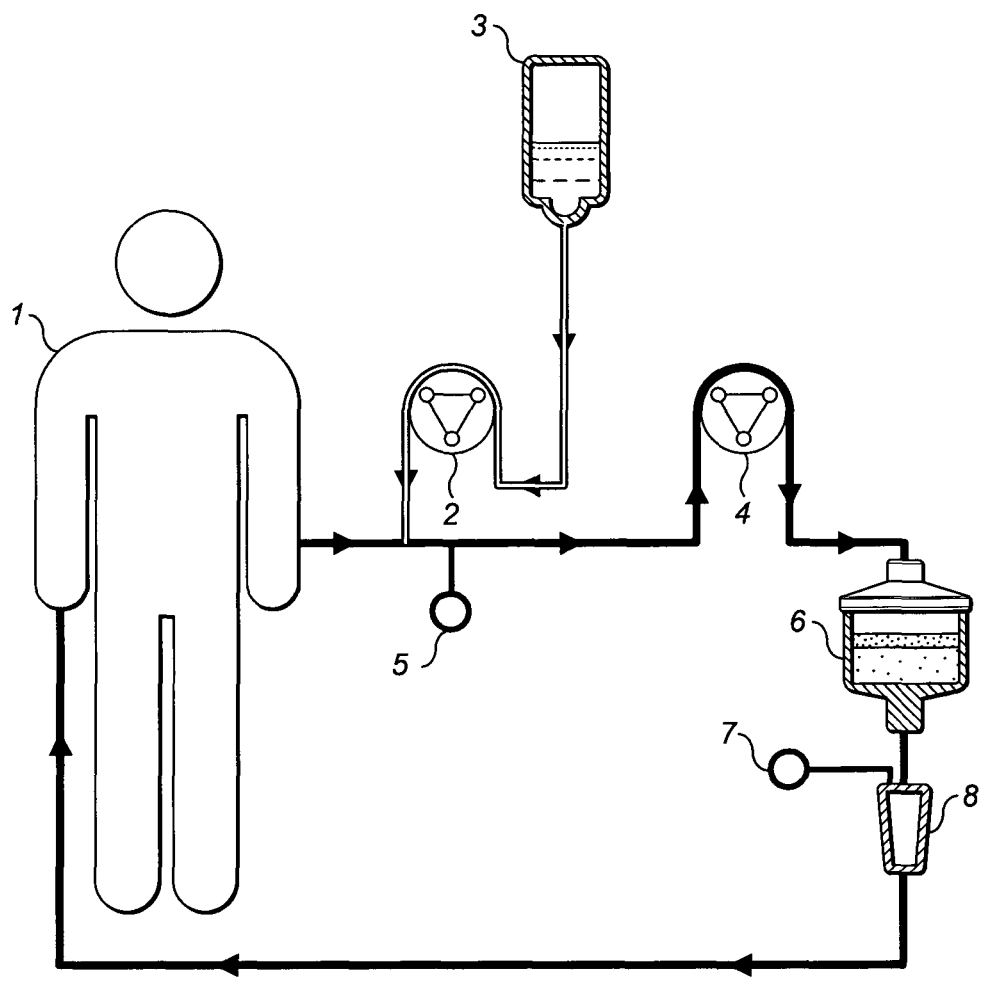
FIG. 5—The overall leukapheresis system

Column Design and Properties
Introduction
Apheresis is an established treatment used for depletion of blood components, such as antibodies, low-density lipoproteins (LDL) and blood cells. Leukapheresis is the apheresis treatment used for removal of white blood cells, leukocytes. The patient is connected to an extracorporeal blood circulating system; the blood is drawn from a vein in one arm, passed through a column device and returned into the other arm of the patient. Side effects of leukapheresis treatments are varying from mild events like headache, dizziness, hypotension, palpitation and flush seen in 0.1 to 5% of treated patients.
The Column
The column is intended to be used as a leukapheresis treatment for IBD. It will specifically remove CCR9-expressing gut-homing leukocytes through the use of a bTECK containing resin, exploiting the CCR9-TECK interaction. The column consists of three combined components, the plastic house, the streptavidin (SA) Sepharose™ BigBeads matrix and bTECK bound to the matrix. The treatment is conducted using the same techniques as a standard apheresis procedure.
The Plastic House (FIG. 4)
The plastic house, designed to keep a continuous blood flow through the matrix, consists of a transparent body and red-coloured top. The top has a distribution plate (2) at the inflow site (1) to spread the blood evenly over the entire matrix area. The plate is the first safety barrier preventing larger particles flowing through the column and into the patient. Safety filter units (3 and 4) are placed at the inflow (1) and outflow (5) sites of the plastic housing. The safety filter unit contains three filters designed to be a robust barrier and stop all particles larger than blood cells passing through the column. The plastic housing design is shown in FIG. 4. The design with safety filters (3 and 4) at both ends of the column device will minimize the risk of leakage of particles into the patient, including in the event that the device is placed up side down with the blood flow in the opposite direction to that anticipated.
Streptavidin Sepharose™ BigBeads
The second component in the device is the affinity matrix called streptavidin Sepharose™ BigBeads (Sepharose™ GE Healthcare, Sweden). Sepharose™ is a cross linked, beaded-form of agarose, which is a polysaccharide extracted from seaweed. Sepharose™ and agarose are commonly used as column matrices in biomedical affinity techniques. It is chosen for its optimal distribution capacity and can provide a large available area for affinity binding.
bTECK
Coupled to the matrix is the third component of the device, the bTECK. This bTECK peptide is a synthetic, engineered version of the human chemokine TECK, which is truncated and biotinylated, but retains its binding activity to the TECK receptor CCR9. By biotinylating the engineered TECK, it is able to bind to the streptavidin molecules in the Sepharose™ matrix. The biotin-streptavidin binding is known be one of the strongest biological interactions with a Kd in the order of $4 \times 10^{-14}$ M. The calculated ratio of streptavidin:biotin binding sites in the column is 10:1. Therefore, the coupling between the matrix and bTECK will be immediate, minimising the risk of bTECK decoupling from the matrix.
The Apheresis System
To conduct the leukapheresis the following components are needed; the column, tubing system, and a 4008 ADS pump (Fresenius Medical Care).
The Circuit
The system is illustrated in FIG. 5. The patient (1) is connected to the extracorporeal circuit via sterile Venflon needles to veins in the right and the left arms. A saline bag (3) is also connected and the saline solution is pumped with an ACD pump (2). Blood is drawn from one arm of the patient through the sterile tubing system by the blood pump (4) and passed through the column (6) and back to the patient. The tubing system is connected to the column via standard dialysis luer-lock couplings. The couplings on the column are colour-coded for correct assembly; red tubing for inflow to the red column top and blue tubing for outflow back to the patient. An air detector (8) is present. Inlet pressure (5) and Pven sensors (7) are employed to monitor the pressure in the circuit.
The 4008 ADS Pump
An apheresis pump, from Fresenius Medical Care, monitors the patient's inflow and outflow, the pressure in the extracorporeal circulation and can discriminate air by a bubble catcher and air detector. A clot catcher filter is placed inside the bubble catcher. The pump also has an optical detector to distinguish between light, e.g. saline solution or air present in the tubing system and dark e.g. blood present in the tubing system.

Figure 6:
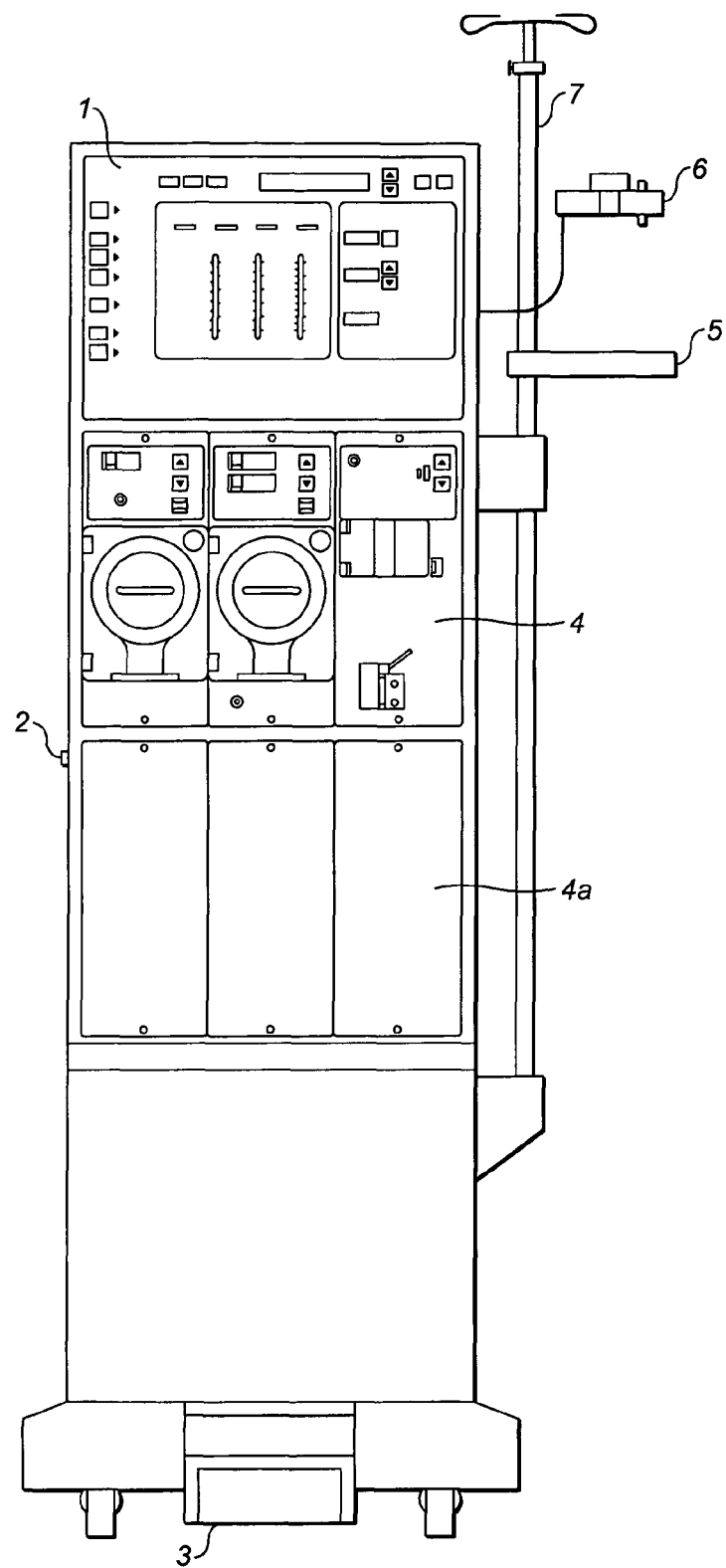
FIG. 6—The pump with air detector and optical detector (4).

A schematic diagram of the pump, showing the air detector and optical filter is shown in FIG. 6. If the pump system detects air bubbles and optical fluctuations or if extracorporeal pressure values are out of the set range, then the pump stops immediately and a visual/audible alarm are emitted.

Legend for FIG. 6:
1. Monitor
2. Holder for waste bag
3. Modules (left to right—Blood pump, ACD pump, Air detector)
4. Reserve places for further modules
5. Absorber holder
6. Drip detector
7. IV pole Preparation of the Patient The patient will be administered anticoagulants prior to each treatment session. A sterile saline solution with 5000 IE Heparin will be used for priming the extracorporeal system, thereafter a bolus injection with 4000 IE Heparin will be added into the circuit at the start of each treatment session.

Leukapheresis Time and Flow Rate

The apheresis system should be operated at a flow rate of 30-60 mL/min. A treatment is finalised after 1800 mL of blood has been circulated.

Storage Conditions

The column devices should be stored between 1 and 25° C. avoiding freezing and more elevated temperatures. Stability data>3 months indicate no difference in functionality over time or by temperature (room temperature and refrigerated). The columns will be kept in refrigerated conditions until use. Mechanical damage as those resulting from violent vibrations and trauma should be avoided. Column stored outside of these recommendations should not be used.

Transport Conditions

The column devices will be transported under refrigerated condition, avoiding freezing and more elevated temperatures. Mechanical damage such as those resulting from violent vibrations and trauma should be avoided.

Example 10

Non-Clinical Studies

Introduction

As early as the 1970's the observation was made that lymphocytes harvested from mesenteric lymph nodes in donor sheep were accumulated in the intestine after transferral to recipient animals (4, 5). These initial animal studies suggested a specific homing capability of circulating lymphocytes targeted for different compartments in the body. Further studies in murine models demonstrated several signalling pathways responsible for the organ specificity of different T-cell subsets. L-selectin (also known as CD62L) was shown to be a cell surface protein responsible for the migration of lymphocytes to the mesenteric lymph nodes (6). In the endothelial lining of the intestinal blood vessels, MadCAM1 and TECK were found to be engaged in the adherence and transmigration of mucosa-bound lymphocytes and monocytes. The studies drew the attention to the corresponding receptors of the immune cells, alpha4beta7 and CCR9 respectively (2). In this context, one of the mouse models for Crohn's disease, TNFDeltaARE, suggested that the alpha4beta7 pathway worked independently from the TECKCCR9-dependent transit and seemed to be the major mechanism behind gut-homing (7, 8). However, other mouse models have established the TECK-CCR9 interaction as equally important in terms of gut-homing to the inflamed mucosa. TECK−/− and CCR9−/− murine models as well as antibody-mediated inhibition of TECK-CCR9 binding demonstrate attenuated mucosal inflammation (9-12). Hence, the influence of the different homing mechanisms appears to be dependent on the animal model of choice. Several studies in murine models have indicated a preference of the CCR9-expressing T-cells to the small intestine. However, mucosal inflammation restricted to the colon as seen in the ulcerative colitis mouse model MDR1a−/−, exhibits a dependency on CCR9-expressing lymphocytes. After administration of the CCR9-blocking protein CCX282-B, the inflammatory lesions in the colon are clearly resolved, suggesting an important role for the TECK-CCR9 interaction also in the colonic mucosa (3). The therapeutic implications of the TECK-CCR9 homing mechanism have resulted in several human studies, and as seen in mice, CCR9-expressing T-cells have been found to accumulate in the human small intestine (2, 3, 13). In patients with CD, there is a significant increase of CCR9-expressing lymphocytes in the mesenteric lymph nodes compared to healthy controls (13).

Additional studies have described TECK and the presence of CCR9-expressing T-cells in the inflamed mucosa of the colon in patients suffering from CD or UC. Healthy controls have also been shown to have CCR9-expressing immune cells in the colonic mucosa, establishing an important role for this receptor in the normal function of the gut-associated immune system (3). In the context of inflammatory bowel disease, the animal models available do not correspond particularly well to the human intestinal inflammation. Therefore the focus has been on the use of in-vitro experiments on blood samples from IBD patients for non-clinical proof of concept testing. In addition, the bTECK protein used in the leukapheresis column is specific to the human CCR9 surface protein, which limits the feasibility of in-vivo animal efficacy studies.

In-Vitro Depletion of Target Cell Populations

To investigate the ability to eliminate CCR9-expressing cells, in vitro tests have been performed on the bTECK coupled matrix. Blood was collected from blood donors and IBD patients and passed through the column device containing bTECK coupled matrix. Blood samples were taken before and after column passage and analyzed by flow cytometry (FACS) for the depletion of CCR9-expressing cells.

Figure 7:
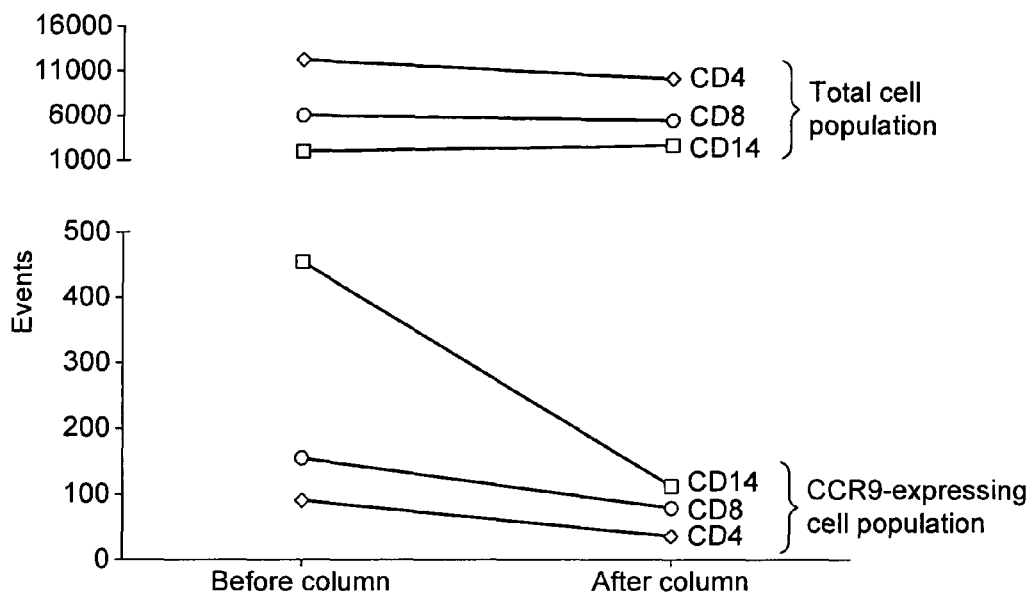
FIG. 7—Depletion of CCR9-expressing cell populations in one blood donor. Total cell populations are unaffected after the column passage.
Figure 8:
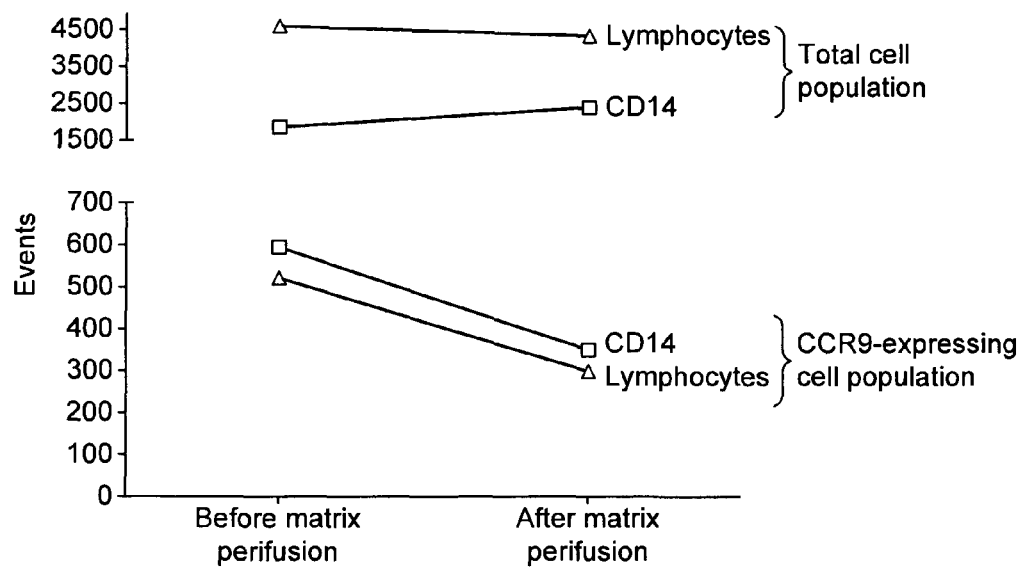
FIG. 8—Depletion of CCR9-expressing cell populations in one IBD patient. Total cell populations are unaffected after the column passage.

The results demonstrate significant depletion of the target population CD14-positive CCR9-expressing cells post matrix perfusion; while total CD14-positive cells remain unchanged. Depletion tests were performed on blood from healthy donors and IBD patients confirming similar effects. The results are shown in FIGS. 7 and 8 respectively.

In conclusion, the in-vitro results demonstrate a specific reduction of 50-75% of the CCR9-expressing cells by the column. Non-CCR9-expressing cells remained unaffected.

Example 11

Toxocological Evaluation and Safety Testing

Exposure

The exposure of the patient by the column device can take place in two different ways. Firstly, locally of the blood and its cells, to chemicals including bTECK in the device and secondly systemically to chemicals including bTECK released from the device and administered to the patient via the returning blood. In both cases there are limited possibilities to assess the total exposure but studies of the matrix stability would reveal systemic exposure to Sepharose, Streptavidin and bTECK, see below. However, as the plastics and filter material meet the FDA/ISO 10993 standard and USP class VI biological evaluation requirements, even after sterilisation by irradiation, it can be concluded that the exposure of toxic compound from these parts of the device is negligible. Furthermore there are no data to suggest any interaction between the different components of the column.

Stability of the Matrix

Stability properties of the matrix were studied to evaluate if any leakage of material occurs during active tests on the column. A matrix filled column was rinsed in the pump system with 2 L PBS (phosphate-buffered saline), in 30-100 ml/min to wash off residual particles from manufacturing step. Samples of fluid before and after the column were collected and analysed by microscope and ELISA for leakage of products.

No visible leakage of matrix material after rinsing through the column with 2 L PBS was observed.

Binding stability was tested with ELISA. To detect detached bTECK we incubated wells with a Streptavidin antibody for 1 h in 4° C. To detect detached streptavidin we incubated wells with biotinylated peroxidase for 1 h at room temperature. Results of the studies showed no leakage of Sepharose particles, Streptavidin or bTECK from the matrix.

Biological (Toxicological) Data

The desired biological effect, specific removal of activated leukocytes targeted at the gastrointestinal tract (gut-homing cells), is caused by bTECK attracting and binding to its specific receptor CCR9 on cells by a strong receptor-ligand affinity. Blood cells not expressing the receptor pass through the column and are returned to the patient. The exposure at the intended use of the column might also cause various adverse biological (toxic) effects, which have to be evaluated according to ISO 10993-1 of this category of medical device. Based upon the assumed local exposure when the blood is distributed homogeneously over the column area it is possible that the blood, particularly its cells, could be adversely affected. The chemokine bTECK or any chemical in the device might cause local effects such as cytotoxicity and haemoincompatibilities. Furthermore it is of utmost importance to investigate any activation of immune cells. The patient will also be systemically exposed to bTECK or any chemical released from the column device or the plastic tubing during the perfusion, which might result in biological (toxicological) effects. These chemicals might cause various systemic effects of which cytotoxicity, sensitisation, irritation and intracutaneous reactivity, systemic toxicity (acute), subacute and subchronic toxicity and haemoincompatibilities should be evaluated according to ISO 10993-1. In order to establish the biological effect of bTECK, synthesised as a truncated version of 9 kDa and biotinylated, different studies have been performed.

Specific cell depletion and analysis by FACS (Fluorescent activated cell sorting) in vitro For cell depletion tests with matrix and bTECK on IBD patient blood, a small-scale tool to simulate the process in a full size column device was used. The simulation was made with nylon filter set on top of a plastic tube. The blood was gently mixed with matrix and passed through the filter into the collecting tube. Samples of unfiltered blood and filtered blood were lysed before being stained with antibodies and further analysed with FACS.

Blood samples from blood donors were collected and cell depletion test were performed with the column prototype containing bTECK coupled matrix. Samples were taken before and after column passage and lysed before being stained with antibodies and further analysed with FACS.

Specific depletion of bTECK receptor expressing cells was successful in both the small-scale tool as well as in the column device prototype. It could also be shown that the depletion was specific on CCR9-expressing cell populations. For example in FIGS. 8 and 7 the CCR9 positive cells CD14 and lymphocytes cells (CD4 and CD8) are highly reduced, less than ⅕ passed through the column, while total counts of CD14 and lymphocyte populations were unchanged after passing through the column.

Activation, Proliferation and Cell Death

The aim was to study activation and functional properties of cells that have passed through the column device.

Activation Markers

Figure 9:
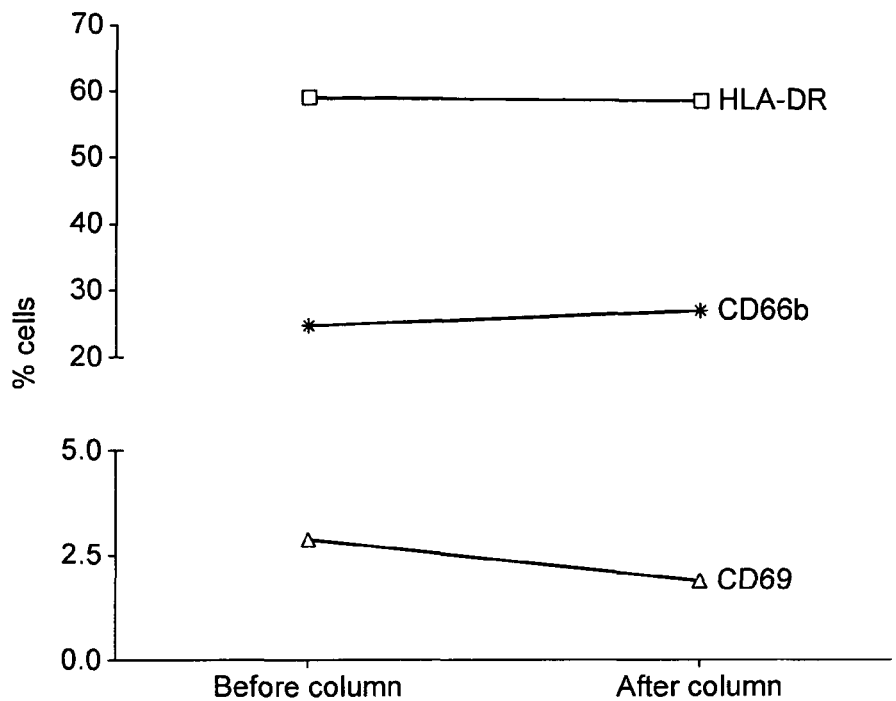
FIG. 9—Activation markers on blood cells from one blood donor before and after column passage.

The lysed cells were incubated for 15 min at room temperature with 10% HUS (human antibody serum) to prevent nonspecific binding to cells with Fc-receptors on its cell surface. Cells were stained for activation markers; CD69 (lymphocytes), CD66b (granulocytes) and HLA-DR (monocytes). Cells were collected on a FACSAria and analysed by FACS-Diva Software. The number of the studied cells with activation markers was the same after the column passage as before (see FIG. 9).

Cytokine Release

Figure 10:
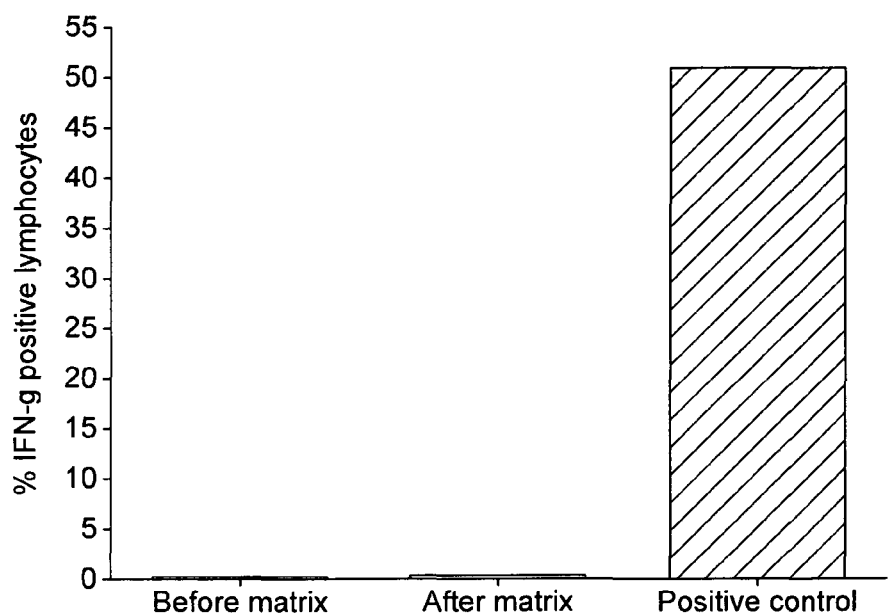
FIG. 10—IFN-γ secretion on cells before and after passing the small-scale tool.

An inflammatory cytokine release test, Interferon gamma (IFN γ) Secretion Assay kit, was used to study activation of cells before and after contact with the matrix. The secretion test will show the amount and what phenotype of cells that produces IFN γ after stimulation. Peripheral mononuclear blood cells (PBMC) from 4 blood donors were Ficoll separated. Cells were resuspended in cell culture medium (RPMI with 1% Pest+1% L-Glut+5% HUS) in a concentration of $1 \times 10^6$ cells/ml. The matrix was washed with PBS and mixed with 0.1 µg/ml bTECK. Half of the cell suspension was passed through a small-scale tool with matrix. Unfiltered and filtered cells were added in 500 000/well in a 48 well plate and incubated for 16 hours 37° C. PMA (50 ng/ml)+Ionomycin (1 µg/ml) was added to cells as a positive control. After 16 hours cells were analysed for amount of surface bound and secrete IFN γ Other Mabs for FACS analysis were CD3, CD14 and DAPI. There was no significant change in the IFN γ secretion (see FIG. 10).

Proliferation Assay with [3H] Incorporation

Figure 11:
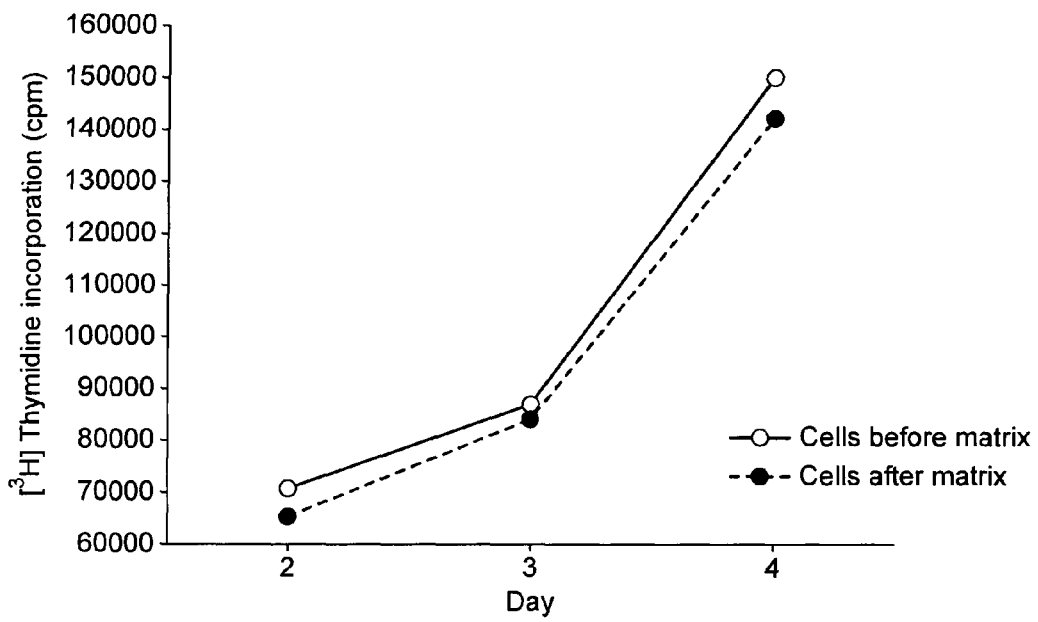
FIG. 11—Result on PHA antigen stimulating cells, before and after passing through the column FIG. 12—Results on cell death after cells incubated with high concentrations of bTECK FIG. 13—HPLC of purified folded Biotin-TECK(Nleu).

PBMC from heparinised whole blood from one blood donor was isolated and prepared by Ficoll separation. Cells were counted and diluted $2 \times 10^6$ cells/ml cell culture medium (RPMI+10% BGS+1% pest and 1% L-glut). Half of the cell suspension was passed through a small scale tool with matrix (SA conc 4 mg/ml) coupled with 200 nM (0.2 µg/ml) of bTECK. 50 µl/well from $2 \times 10^6$ cells/ml cell suspension (100 000 cells) were added in triplicate to a 96-well plate according to protocol. 50 µl/well of cell culture medium was used as a negative control and 50 µl/well PHA (phytohemagglutinin) antigen (5 µg/ml) as positive control. Cells were incubated in 37° C. until day 2, 3 and 4. Before harvest of cells 25 µl of thymidine [3H] was added to wells and further incubated in 37° C. for 18 h. After 18 h the cells were harvested and incorporated [3H] is counted in a scintillator. [3H] incorporation as a sign of proliferation was the same in cells after passing through the column as before (see FIG. 11).

Cell Death-Apoptosis Assay with Annexin V

Figure 12:
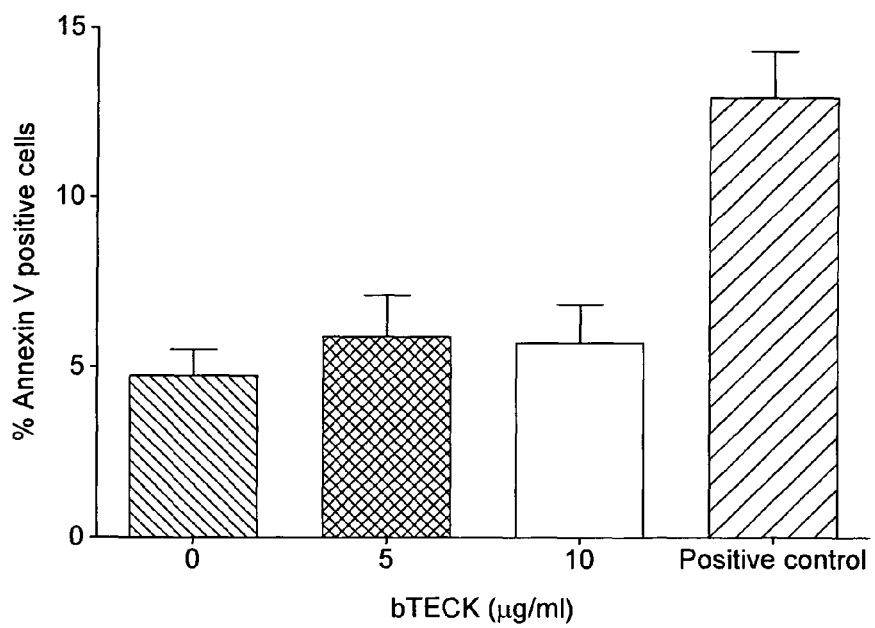

PBMCs were isolated from 3 blood donors by Ficoll separation. The cells were washed twice with PBS and resuspended in culture media (RPMI with 1% L-glut, 1% pest and 10% BGS) in concentration of $1 \times 10^6$/ml. Cells were stimulated with 5 µg/ml or 10 µg/ml bTECK. Cells were incubated for 16 h in a 24-well plate. As a positive control we used Dexametason (1 µM). Cells were washed two times in PBS and dyed with Annexin V according to BD Annexin V kit protocol. Before FACS analysis 100 µl DAPI was added to the cells. Samples were analysed on FACS Aria with FACS Diva software. Apoptopic cells defined as Annexin V positive and DAPI negative. The number of Annexin V positive cells was not significantly increased after exposure to 5 or 10 µg/ml bTECK (see FIG. 12).

Summary

Studies were made on cells before and after being passed through a column device or after direct contact with bTECK coupled Streptavidin Sepharose matrix. Results showed no or minor effects on cells that have been in contact with matrix and bTECK. The number of cells CD69 (lymphocytes), CD66b (granulocytes) and HLA-DR (monocytes). with activation markers was the same after passage of the column as before. The ability of PBMC to proliferate was not affected and the amount of cytokine releasing cells was low. High amount of bTECK, 5-10 times more than will be used in the initial clinical study column device, showed a minor effect on cell death.

Toxicological Studies

In Vitro Cytotoxicity Assay

The column matrix was tested for in vitro cytotoxicity in cultured mammalian cells (L 929 mouse fibroblasts). The test was performed in accordance with the ISO 10993-5 Elution Test guideline. The test item was supplied as a slurry of coated agarose beads in 20% ethanol. The agarose beads were washed and then resuspended in the same volume of sterile isotonic saline solution (0.9% NaCl) to remove the ethanol before testing, as the column matrix will be washed before the intended use. An extract of the column was prepared by incubating the washed test item in complete cell culture medium (HAM F12 medium with 10% foetal bovine serum and 50 µg/ml gentamycin) for 24 hours at 37° C. with gentle mixing. An extraction ratio of 0.2 ml test item/ml medium (ca. 0.2 g/ml) was used. The extract was tested undiluted as well as diluted 1+3 in fresh cell culture medium. Negative controls (polypropylene extract, 6 cm$^2$/ml), positive controls (tin-stabilised polyvinyl chloride extract, 0.3 cm$^2$/ml) and untreated control cultures treated with complete cell culture medium were included. Triplicate cell cultures were treated at each test point for 48 hours. The control treatments produced appropriate responses, demonstrating the correct functioning and sensitivity of the test system. The undiluted extract and the diluted extract of the column both showed no toxicity (cytotoxicity grade 0).

Hemolysis Test

The column matrix was tested for in vitro hemolysis activity (lysis of erythrocytes). The test for hemolysis was performed as required by the ISO 10993-4 guideline. The test was designed in accordance with the recommendations from the Material Science Institute (MSI), Tennessee, USA (1979), with the test item in direct contact with a dilute mixture of rabbit blood in sterile saline solution. The test item was supplied as a slurry of coated agarose beads in 20% ethanol. The agarose beads were washed and then resuspended in the same volume of sterile isotonic saline solution (0.9% NaCl) to remove the ethanol before testing, as the column matrix will be washed before the intended use. The test item was placed in sterile isotonic saline solution using a ratio of 0.2 ml of the test item/ml saline (ca. 0.2 g/ml). After incubation for 39 minutes at 37° C., rabbit blood (20 µl blood/ml saline) was added and the incubation was continued for a further 60 minutes. Negative controls (isotonic saline) and positive controls (distilled water) were included. All treatments were performed in triplicate. At the end of the incubation period, the mixtures were centrifuged for 5 minutes at 500×g. Then the absorbance of the supernatant liquids was measured at 545 nm. The percentage of hemolysis was calculated. The mean amount of hemolysis observed in the blood samples treated with the column matrix under the conditions employed in this study was −0.3%. It is concluded that the column matrix passes the MSI hemolysis test requirements (hemolysis<5%).

Coagulation Test in Human Blood

The column matrix was tested for its ability to affect the rate of coagulation of samples of human blood in vitro. The test item was supplied as a slurry of coated agarose beads in 20% ethanol. The agarose beads were washed and then resuspended in the same volume of sterile isotonic saline solution (0.9% NaCl) to remove the ethanol before testing, as the column matrix will be washed before the intended use. A sample of the washed test item (0.2 ml) was placed into a test tube. Negative control (untreated) and positive control (Fuller's Earth) test tubes were also prepared. Fresh human blood (1 ml) was added to each tube. The ratio for the test item was approximately 0.2 ml test item per ml blood (ca. 0.2 g/ml). The tubes were placed in a water bath at approximately 37° C. and shaken regularly. The time taken for total coagulation of the blood was recorded. The test item and each control were testedonce with blood from each of four people. Results from the control treatments demonstrated the efficacy and sensitivity of the test system.

The mean coagulation time of blood treated with the matrix showed a small reduction to 91% of the mean negative control value. However, the reduction is not considered significant because of the great the inter-individual variation in the test between the four donors. It is concluded that the column matrix did not affect the coagulation time of human blood in this test.

Summary

Based on the results of the tests performed and the evaluations of the column it can be concluded that has a very low toxicity, no specific type of toxicity or target organ have been identified.

Example 12

TECK-PEG-Biotin Synthesis Summary

Target Molecule:

TECK (Met to Nleu substitution) derivatised at the ε-amino side chain functionality of Lys72 with PEG-Biotin (TFA salt)

Modifications:

Truncated form of human TECK corresponding to residues 1-74 of the mature protein, which encompasses the sequence corresponding to the chemokine fold. The full length mature protein is 127 amino acids (the signal peptide is 23 amino acids in a 150 amino acid immature protein). The single methionine within the sequence was altered to Norleucine, to mitigate against oxidation of this residue during the chain assembly, which was observed during the synthesis of the natural sequence derivative. The Gln at the N-terminus of the proteins is subject to pyroGlu formation under physiological conditions. Thus Gln1 of the sequence was substituted with pyroglutamine to prevent mixed species of N-terminal Gln and pyroGlu being generated. This improves the yield of synthesis and ensures a homogeneous chemokine preparation through column manufacture and use. The naturally occurring lysine at position 72 was modified through biotinylation on the resin. A PEG spacer was incorporated between the ε-amino functionality and the biotin.

The linear amino acid sequence (SEQ ID NO:1) is shown, prior to attachment of the PEG spacer and biotin molecules at amino acid 72 (K):

H-PyrGVFEDCCLAYHYPIGWAVLRRAWTYRIQEVSGSCNLPAAIFYL

PKRHRKVCGNPKSREVQRANleKLLDARNKVF-OH

The engineered TECK sequence was assembled on a solid support, using Fmoc protocols for solid-phase peptide synthesis:

H-PyrGVFEDCCLAYHYPIGWAVLRRAWTYRIQEVSGSCNLPAAIFYL

PKRHRKVCGNPKSREVQRANleKLLDARNK(Dde)VF-RESIN

FmocLys(Dde)-OH was incorporated as residue 72 to facilitate site-specific labelling at this position of the protein.

Met to Nle substitution.

N-terminal Gln to pyroglutamic acid substitution.

Removal of Dde Protection:

The Dde protecting group was removed by treatment of all resin (2.5 g) with a solution of 2% hydrazine in DMF (100 ml) over 1 hour period to afford 2.0 g resin.

Labelling Steps:

1. Couple Fmoc-8-amino-3,6-dioctanoic acid

Resin (1.5 g) was swollen in DMF (2 ml) and then a solution of Fmoc-8-amino-3,6-dioctanoic acid (0.38 g, 1 mmol), DIC solution (2 ml, 0.2M in DMF) and HOCt solution (2 ml, 0.2M in DMF) was added. The mixture was sonicated for 2 hours and then washed with DMF.

2. Cap

The resin was capped with 0.5M acetic anhydride/DMF solution (20 ml) for 5 minutes and then washed with DMF.

3. Fmoc Deprotection

Fmoc deprotection was carried out by treatment with 20% piperidine in DMF solution (2×50 ml) for 15 minutes each. The resin was washed with DMF.

4. Couple Biotin-OSu

A solution of Biotin-NHS ester (341 mg, 1 mmol) and DIPEA (348 ul) in DMF (10 ml) was added to the resin and the mixture was sonicated for 3 hours. The resin was washed thoroughly with DMF and DCM then dried in vacuo. Dry resin obtained=1.5 g.

Cleavage:

Dry peptide resin (1.5 g) and the mixture was cleaved with TFA (30 ml) containing a scavenger cocktail consisting of TIS, thioanisole, water, EDT and phenol and the mixture was stirred at room temperature for 6 hours. The solution was filtered into cold ether and the resin rinsed with TFA. The peptide was centrifuged, washed with ether, centrifuged and lyophilised to give 1.0 g crude peptide.

Folding Protocol:

Crude peptide (100 mg) was dissolved into 6M GnHCl (233 ml) and then rapidly diluted to 2M GnHCl concentration by the addition of 50 mM TRIS pH8 (467 ml) containing 0.5 mM GSSG and 5 mM GSH. The mixture was stirred at room temperature for 2.5 days and then analysed by HPLC (Jupiter C18, 250×4 6 mm column, 10-60% B over 30 minutes. HPLC analysis confirmed the formation of desired product as well as mis-folded by-products.

Purification:

The folded protein was purified by reverse phase HPLC using a Jupiter C18, 250×21 mm column, 9 ml/min, 10-60% B over 50 minutes. 11.1 mg of pure folded Nle-TECK-Biotin was afforded.

Figure 13:
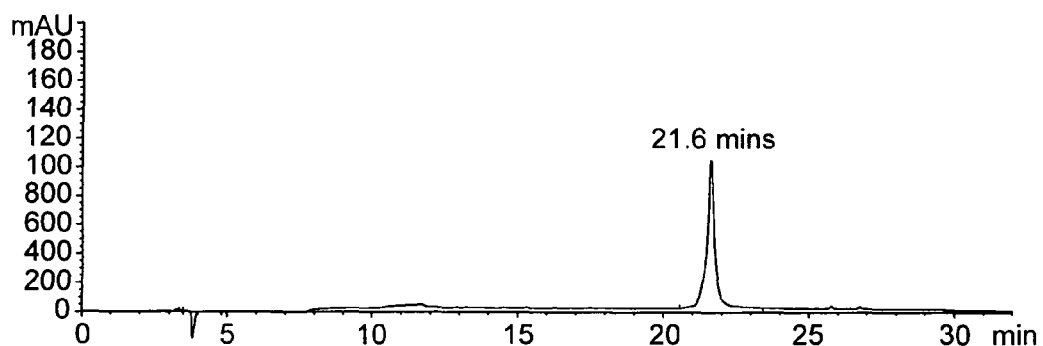

FIG. 13 shows HPLC of purified folded Biotin-TECK (Nleu). The protein eluted in a single peak at 21.6 mins.

Figure 14:
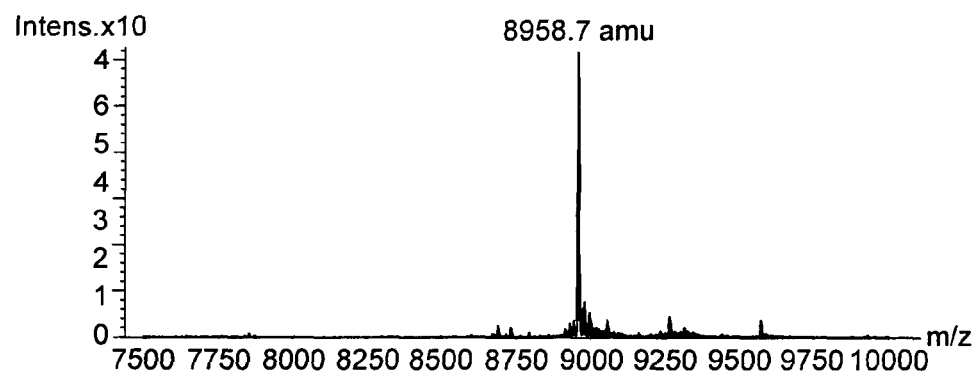
FIG. 14—Electrospray ionisation with tandem mass spectrometry (ES/MS) data of purified folded Biotin-TECK (Nleu).

FIG. 14 shows Electrospray ionisation with tandem mass spectrometry (ES/MS) data of purified folded Biotin-TECK (Nleu). The expected mass was 8959.4 Da.

Functional Assay Data:

TECK-Biotin-Nle was tested for agonist activity in an Aequorin assay against hCCR9 (Euroscreen) and an EC50 value of 63.6 nM was reported. c.f. EC50 for native TECK is 67.87 nM.

REFERENCES

1. Fitzgerald K A, Oneill L A J, Gearing A J H, Canard R E. The Cytokine facts book; 2001.
2. Johansson-Lindbom B, Agace W W. Generation of gut-homing T cells and their localization to the small intestinal mucosa. Immunol Rev 2007; 215:226-42.
3. Walters M J, Berahovich, R., Wang, Y., Wei, Z., Ungashe, S., Lai, N., Ertl, L, Baumgart, T., Howard, M., Schall, T. J. Presence of CCR9 and its ligand CCL25/TECK in the colon: scientific rationale for the use of CCR9 small molecule antagonist COC282-B in colonic disorders. In: UEGW 2008; 2008; 2008.
4. Cahill R N, Poskitt D C, Frost D C, Trnka Z. Two distinct pools of recirculating T lymphocytes: migratory characteristics of nodal and intestinal T lymphocytes. J Exp Med 1977; 145(2):420-8.
5. Hall J G, Hopkins J, Orlans E. Studies on the lymphocytes of sheep. III. Destination of lymph-borne immunoblasts in relation to their tissue of origin. Eur J Immunol 977; 7(1): 30-7.
6. Streeter P R, Rouse B T, Butcher E C. Immunohistologic and functional characterization of a vascular addressin involved in lymphocyte homing into peripheral lymph nodes. J Cell Biol 1988; 107(5):1853-62.
7. Apostolaki M, Manoloukos M, Roulis M, et al. Role of beta7 integrin and the chemokine/chemokine receptor pair CCL25/CCR9 in modeled TNF-dependent Crohn's disease. Gastroenterology 2008; 134(7):2025-35.
8. Staton T L, Habtezion A, Winslow M M, Sato T, Love P E, Butcher E C. CD8+ recent thymic emigrants home to and efficiently repopulate the small intestine epithelium. Nat Immunol 2006; 7(5):482-8.
9. Wurbel M A, Malissen M, Guy-Grand D, Malissen B, Campbell J J. Impaired accumulation of antigen-specific CD8 lymphocytes in chemokine CCL25-deficient intestinal epithelium and lamina propria. J Immunol 2007; 178 (12):7598-606.
10. Wurbel M A, Malissen M, Guy-Grand D, et al. Mice lacking the CCR9CC-chemokine receptor show a mild impairment of early T- and B-cell development and a reduction in T-cell receptor gammadelta(+) gut intraepithelial lymphocytes. Blood 2001; 98(9):2626-32.
11. Johansson-Lindbom B, Svensson M, Wurbel M A, Malissen B, Marquez G, Agace W. Selective generation of gut tropic T cells in gut-associated lymphoid tissue (GALT): requirement for GALT dendritic cells and adjuvant. J Exp Med 2003; 198(6):963-9.
12. Rivera-Nieves J, Ho J, Bamias G, et al. Antibody blockade of CCL25/CCR9 ameliorates early but not late chronic murine ileitis. Gastroenterology 2006; 131(5):1518-29.
13. Saruta M, Yu Q T, Avanesyan A, Fleshner P R, Targan S R, Papadakis K A. Phenotype and effector function of CC chemokine receptor 9-expressing lymphocytes in small intestinal Crohn's disease. J Immunol 2007; 178(5):3293-300.

14. Wang C. et al., *Mucosal Immunol.* 2009 March; 2(2): 173-183.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. An apheresis column loaded with a solid support comprising one or more chemokines immobilized directly or indirectly on the support to permit removal of a cell expressing the cognate receptor of the one or more chemokines from the peripheral blood of a subject.

2. The column of claim 1, wherein said one or more chemokines are biotinylated and wherein the support comprises streptavidin immobilized thereon and wherein the one or more biotinylated chemokines are bound to the streptavidin on the support.

3. The column of claim 1, wherein the support comprises a carbohydrate having a molecular weight of more than 100 kDa, optionally cross-linked.

4. The column of claim 1, wherein the one or more chemokines is selected from the group consisting of CCL25, MIP-Ia, MIP-Ib, MCP-I, MCP-2, MCP-3, MCP-4, TARC, MDC, MIP-3, MIP-3a, MIP3b, MIP-4, 1-309, HCC-I, HCC-2, SLC, IL-8, GROa, GROb, GROg, RANTES, NAP-2, ENA78, GCP-2, IP-IO, MIG, I-TAC, SDF, fractalkine, lymphotactin, eotaxin, eotaxin-2, 1-309, and BLC.

5. The column of claim 4, wherein the one or more chemokines is CCL25.

6. The column of claim 1, wherein the support comprises spheres, beads, or particles of irregular form having an average size from 50 μm to 2 mm.

7. The column of claim 1, wherein the support is treated with an agent to provide the support with anti-coagulation properties.

8. An apheresis column, comprising:
   a solid support comprising streptavidin immobilized thereon; and
   truncated CCL25 chemokine comprising an amino acid sequence 95% identical to the sequence set forth as SEQ ID NO: 1, wherein the truncated CCL25 chemokine is biotinylated to permit immobilization of the CCL25 chemokine on the solid support.

9. The column of claim 8, wherein the truncated CCL25 chemokine is biotinylated at position 72 (lysine) to permit immobilization of the chemokine on a solid support.

10. A method of removing one or more cells expressing a cognate receptor of one or more chemokines from the peripheral blood of a subject, comprising:
    providing the apheresis column of claim 1; and,
    contacting the column with a portion of the subject's peripheral blood, thereby depleting the portion of the subject's peripheral blood of at least one cell expressing a cognate receptor of the one or more chemokines.

11. The method of claim 10, further comprising infusing the depleted blood to the subject.

12. The method of claim 10, wherein the cell is a leukocyte selected from the group consisting of a T lymphocyte, monocyte, neutrophil granulocyte, and an eosinophil granulocyte.

13. The method of claim 10, wherein removing one or more cells expressing a cognate receptor of one or more chemokines from the peripheral blood of a subject is used to treat an inflammatory condition.

14. The method of claim 10, wherein the one or more chemokine is selected from the group consisting of CCL25, MIP-Ia, MIP-Ib, MCP-I, MCP-2, MCP-3, MCP-4, TARC, MDC, MIP-3, MIP-3a, MIP3b, MIP-4, 1-309, HCC-I, HCC-2, SLC, IL-8, GROa, GROb, GROg, RANTES, NAP-2, ENA78, GCP-2, IP-IO, MIG, I-TAC, SDF, fractalkine, lymphotactin, eotaxin, eotaxin-2, 1-309, and BLC.

15. The method of claim 14, wherein the one or more chemokines is CCL25.

16. The method of claim 15, wherein the chemokine is a truncated CCL25 chemokine comprising an amino acid sequence 95% identical to the amino acid sequence set forth as SEQ ID NO: 1.

17. The method of claim 16, wherein truncated CCL25 chemokine is biotinylated at position 72 (lysine) to permit immobilization of the chemokine on a solid support.

18. The method of claim 10, wherein the support has been treated with an agent to provide the support with anti-coagulation properties.

19. A method of removing one or more cells expressing a cognate receptor of one or more chemokines from the peripheral blood of a subject, comprising:
providing the apheresis column of claim 8; and
contacting the column with a portion of the subject's peripheral blood, thereby depleting the portion of the subject's peripheral blood of at least one cell expressing a cognate receptor of the one or more chemokines.

20. The method of claim 19, wherein the support is a heparinized support.

21. The apheresis column of claim 8, wherein the truncated CCL25 chemokine consists of the amino acid sequence set forth as SEQ ID NO: 1.

* * * * *